(12) United States Patent
Borigo et al.

(10) Patent No.: US 10,099,791 B2
(45) Date of Patent: Oct. 16, 2018

(54) MAGNETOSTRICTIVE MULTI-FREQUENCY GUIDED WAVE ICE SENSING PROBE

(71) Applicant: FBS, Inc., Bellefonte, PA (US)

(72) Inventors: Cody J. Borigo, Port Matilda, PA (US); Jason Philtron, State College, PA (US); Alex Reese, Bellefonte, PA (US); Steven E. Owens, Bellefonte, PA (US); Joseph L. Rose, State College, PA (US)

(73) Assignee: FBS, INC., Bellefonte, PA (US)

( * ) Notice: Subject to any disclaimer, the term of this patent is extended or adjusted under 35 U.S.C. 154(b) by 16 days.

(21) Appl. No.: 15/219,524

(22) Filed: Jul. 26, 2016

(65) Prior Publication Data
US 2017/0030848 A1 Feb. 2, 2017

Related U.S. Application Data

(60) Provisional application No. 62/197,651, filed on Jul. 28, 2015.

(51) Int. Cl.
*B64D 15/20* (2006.01)
*B29C 65/00* (2006.01)
(Continued)

(52) U.S. Cl.
CPC .............. *B64D 15/20* (2013.01); *B29C 66/71* (2013.01); *B29C 66/7212* (2013.01);
(Continued)

(58) Field of Classification Search
CPC .. G01R 27/2611; G01N 27/02; G01N 27/025; B29C 66/7212; B64D 15/20
(Continued)

(56) References Cited

U.S. PATENT DOCUMENTS

| | | |
|---|---|---|
| 4,137,470 A | 1/1979 | Désormiére et al. |
| 4,356,731 A | 11/1982 | Mahony |
| | (Continued) | |

OTHER PUBLICATIONS

Hua, Wang, et al. "Establishment and analysis of mathematic model for ice detector." Electronic Measurement and Instruments, 2007. ICEMI'07. 8th International Conference on. IEEE, 2007. APA.*
(Continued)

*Primary Examiner* — Christopher McAndrew
(74) *Attorney, Agent, or Firm* — Duane Morris LLP

(57) ABSTRACT

A system for detecting ice accretion includes a probe body, at least one magnetostrictive guided wave sensor for generating and receiving shear horizontal-type guided waves supported by said probe body, and a controller. The magnetostrictive guided wave sensor includes a ferromagnetic strip, at least one sensor coil disposed adjacent to said ferromagnetic strip, and at least one biasing magnet configured to induce a biasing magnetic field in said ferromagnetic strip. The controller includes a processor in signal communication with the at least one magnetostrictive guided wave sensor. The processor configured to cause the at least one magnetostrictive guided wave sensor to generate guided waves in the body, extract at least one signal feature from a guided wave signal received by the at least one magnetostrictive guided wave sensor, and determine at least one characteristic of ice accreted on an outer surface of said probe body.

21 Claims, 21 Drawing Sheets

(51) Int. Cl.
*G01N 27/02* (2006.01)
*G01R 27/26* (2006.01)

(52) U.S. Cl.
CPC .......... *G01N 27/02* (2013.01); *G01N 27/025* (2013.01); *G01R 27/2611* (2013.01)

(58) Field of Classification Search
USPC ........................................................ 324/654
See application file for complete search history.

(56) References Cited

U.S. PATENT DOCUMENTS

| | | | |
|---|---|---|---|
| 4,461,178 A | 7/1984 | Chamuel | |
| 4,553,137 A | 11/1985 | Marxer | |
| 4,571,693 A * | 2/1986 | Birchak | E21B 47/101 |
| | | | 702/54 |
| 4,604,612 A | 8/1986 | Watkins | |
| 4,913,519 A | 4/1990 | Klainer | |
| 4,980,673 A | 12/1990 | Kleven | |
| 4,996,493 A | 2/1991 | Monat | |
| 5,095,754 A | 3/1992 | Hsu | |
| 5,206,806 A | 4/1993 | Gerardi | |
| 5,260,615 A | 11/1993 | Sahashi | |
| 5,301,905 A | 4/1994 | Blaha | |
| 5,467,944 A | 11/1995 | Luukkala | |
| 5,569,850 A | 10/1996 | Rauckhorst | |
| 5,629,485 A | 5/1997 | Rose | |
| 5,922,958 A | 7/1999 | Schugt | |
| 6,299,703 B1 | 10/2001 | Chen | |
| 6,425,286 B1 * | 7/2002 | Anderson | B64D 15/20 |
| | | | 73/170.26 |
| 6,731,225 B2 | 5/2004 | Vopat | |
| 6,879,168 B2 | 4/2005 | Baas | |
| 7,026,943 B2 | 4/2006 | Knowles | |
| 7,439,877 B1 | 10/2008 | Jarvinen | |
| 7,586,419 B2 | 9/2009 | Ikiades | |
| 7,683,791 B2 | 3/2010 | Gaultieri | |
| 8,060,334 B1 | 11/2011 | Jarvinen | |
| 2002/0105324 A1 * | 8/2002 | Kwun | G01N 29/11 |
| | | | 324/240 |
| 2004/0095137 A1 * | 5/2004 | Kwun | G01N 29/11 |
| | | | 324/240 |
| 2009/0021253 A1 * | 1/2009 | Kwun | G01N 29/043 |
| | | | 324/238 |
| 2013/0069639 A1 * | 3/2013 | Cobb | G01R 33/18 |
| | | | 324/209 |
| 2013/0335075 A1 * | 12/2013 | Davis | G01R 33/1215 |
| | | | 324/239 |

OTHER PUBLICATIONS

Hua, Wang, et al. "Establishment and analysis of mathematic model for ice detector." Electronic Measurement and Instruments, 2007. ICEMI'07. 8th International Conference on. IEEE, 2007.*

Gao, Huidong, and Joseph L. Rose. "Ice detection and classification on an aircraft wing with ultrasonic shear horizontal guided waves." IEEE transactions on ultrasonics, ferroelectrics, and frequency control 56.2 (2009): 334-344.*

Rose, J.L., Ultrasonic Guided Waves in Solid Media, Cambridge University Press, (2014): 1-15, 269-275.

Trémolet de Lacheisserie, E., Magnetostriction: Theory and Applications of Magnetoelasticity, CRC press, (1993): 339-352, 359-361, 198.

Gao, H. et al, "Ice Detection and Classification on an Aircraft Wing with Ultrasonic Shear Horizontal Guided Waves", IEEE Transactions on Ultrasonics, Ferroelectrics, and Frequency Control, Feb. 2009, 56(2):334-344.

Gent, R.W. et al., "Aircraft Icing", Philosophical Transactions of The Royal Society of London Series A, Nov. 2000, 358:2873-2911.

Joule, J.P., "On the effects of magnetism upon the dimensions of iron and steel bars," Phil. Mag., Series 3, 30(199), pp. 76-87, 1842.

Kuokkala, V.T. and Schwarz, R.B., "The use of magnetostrictive film transducers in the measurement of elastic moduli and ultrasonic attenuation of solids," Rev. Sci. Instrum., 63(5), pp. 3136-3142, 1992.

Thomas, S., et al., "Aircraft Anti-Icing and De-Icing Techniques and Modeling", Journal of Aircraft, Sep. 1996, 33(5):841-854.

* cited by examiner

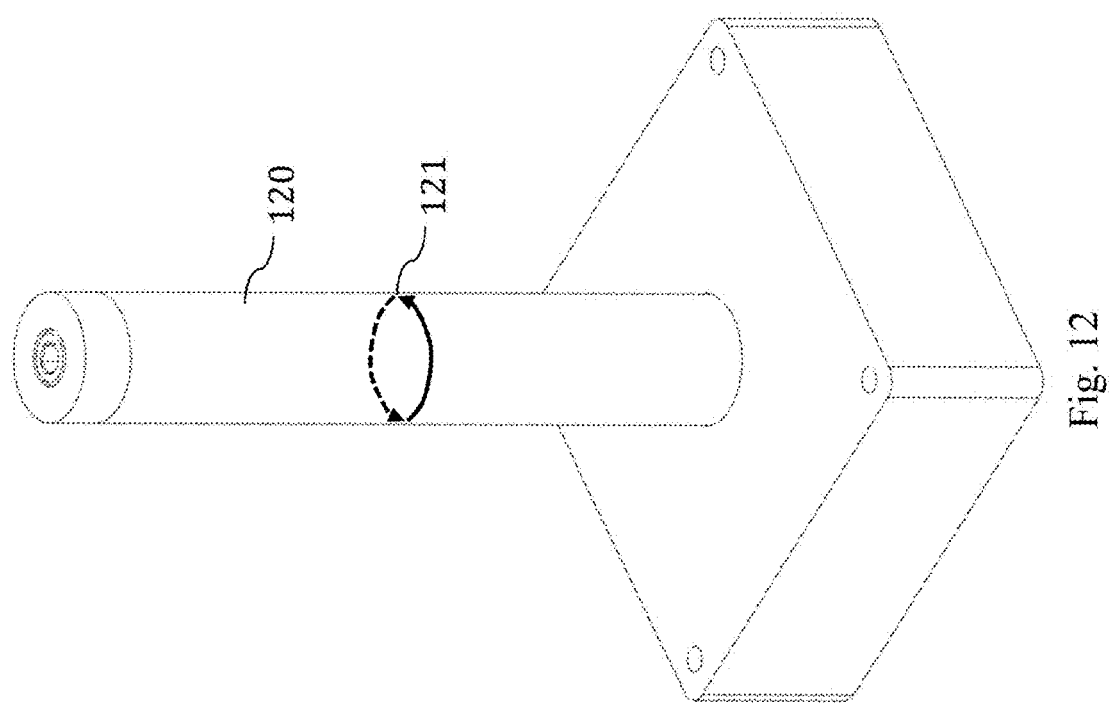

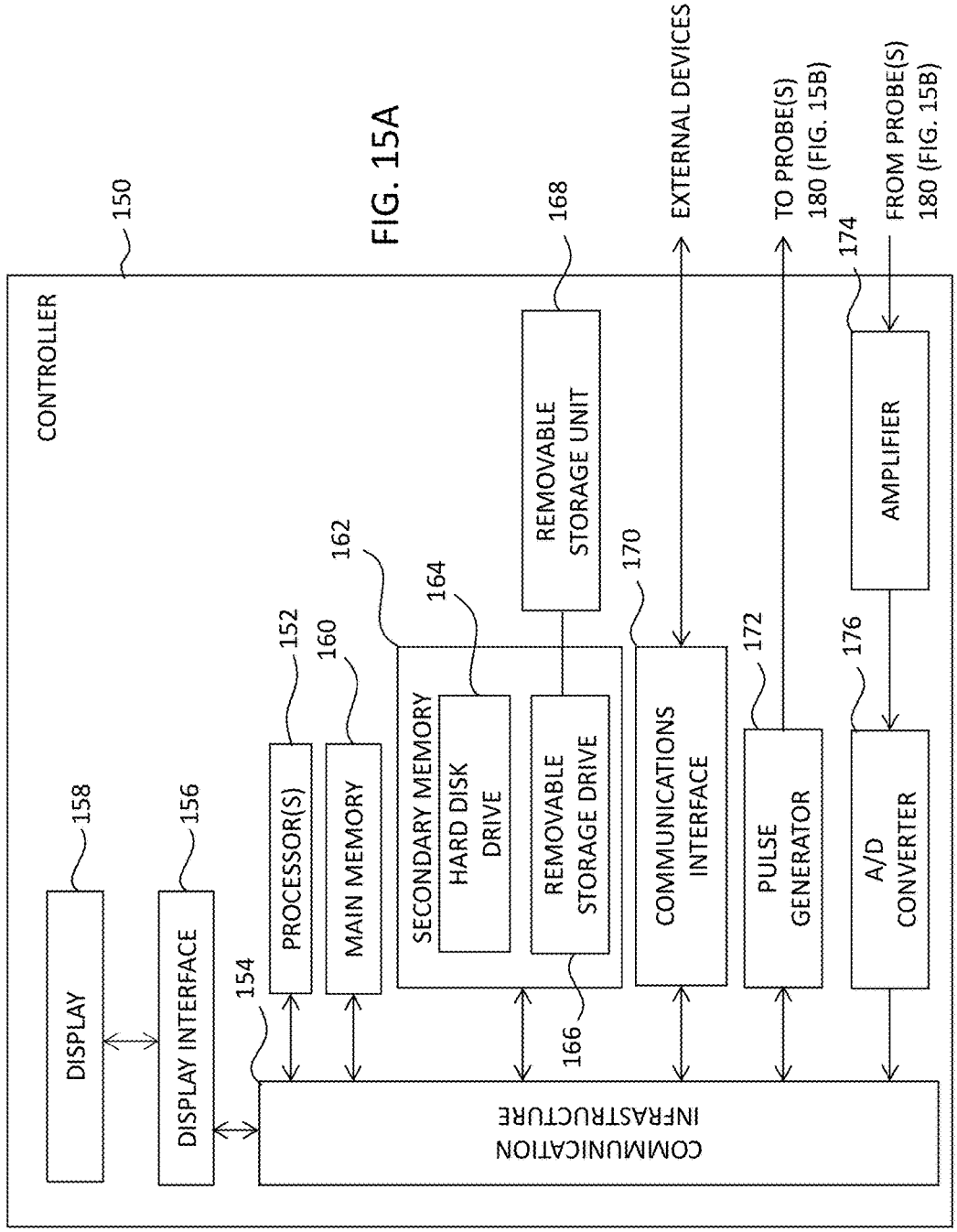

MAGNETOSTRICTIVE MULTI-FREQUENCY GUIDED WAVE ICE SENSING PROBE

CROSS-REFERENCE TO RELATED APPLICATIONS

This application claims priority to U.S. Provisional Patent Application No. 62/197,651, filed Jul. 28, 2015, and entitled "MAGNETOSTRICTIVE MULTI-FREQUENCY GUIDED WAVE ICE SENSING PROBE," which is incorporated by reference herein in its entirety.

FIELD

The disclosed systems and methods relate to the detection of ice accretion on aircraft and other engineered structures for which ice detection is desired.

BACKGROUND

Aircraft icing poses a critical threat to civilian and military fixed-wing aircraft and rotorcraft, particularly when this icing occurs on engine inlets, control surfaces, windshields, rotor blades, and wing leading edges. The hazards of icing arise in several forms including direct concerns such as altered aerodynamic properties, the obstruction of flaps and other mechanical systems, and mass imbalance, as well as indirect concerns such as decreased controls sensitivity, shedding, excessive vibration, and increased power demands. Any one of these complications could potentially lead to an accident.

A wide variety of ice detection systems are currently being utilized or have been utilized for in-flight ice detection in the past. The ice detection methods employed by these systems include external vibrating probes, radioactive probes, fiber optic sensors, temperature probes, electrical resistance or impedance measurements, piezoelectric vibration sensors, differential air pressure detectors, RF transmission line sensors, combined thermal and electrical external measurement probes, acoustic cavity resonators, traditional ultrasonic bulk wave sensing systems, and several ultrasonic guided wave ice sensing systems. Each of the existing ice detection technologies have inherent disadvantages including, but not limited to, insufficient sensitivity, high cost, false alarms due to contamination, hazardous materials, and limited sensing area.

SUMMARY

In some embodiments, a system for detecting ice accretion includes a probe body, at least one magnetostrictive guided wave sensor for generating and receiving shear horizontal-type guided waves supported by said probe body, and a controller. The magnetostrictive guided wave sensor includes a ferromagnetic strip, at least one sensor coil disposed adjacent to said ferromagnetic strip, and at least one biasing magnet configured to induce a biasing magnetic field in said ferromagnetic strip. The controller includes a processor in signal communication with the at least one magnetostrictive guided wave sensor. The processor configured to cause the at least one magnetostrictive guided wave sensor to generate guided waves in the body, extract at least one signal feature from a guided wave signal received by the at least one magnetostrictive guided wave sensor, and determine at least one characteristic of ice accreted on an outer surface of said probe body.

In some embodiments, a method for the detection of ice accretion is provided. The method includes generating a time-varying current in at least one magnetostrictive coil to induce a time-varying magnetization in a ferromagnetic strip in the presence of a biasing magnetic field to generate shear horizontal-type guided waves in a body of a probe supporting the at least one magnetostrictive coil, the ferromagnetic strip, and a biasing magnet; detecting a guided wave signal by the at least one magnetostrictive coil; extracting at least one signal feature, including at least one of optimum transmission frequency, wave packet arrival time, and wave attenuation, from the guided wave signal; and correlating said at least one signal feature with at least one characteristic of ice accreted on an outer surface of said probe.

In some embodiments, a magnetostrictive ultrasonic guided wave sensing system for the detection of ice accretion on aircraft and other engineered structures comprises a probe body; at least one magnetostrictive guided wave sensor for generating and receiving shear horizontal-type guided waves, said sensor including a ferromagnetic strip coupled to the inner surface of said probe body, at least one sensor coil configured to be adjacent to said ferromagnetic strip, and at least one biasing magnet configured to induce a biasing magnetic field in said strip. An electronic pulser system is configured to generate an alternating current in said at least one sensor coil to generate ultrasonic shear horizontal-type guided waves in said probe body. An electronic receiver system is configured to detect said guided waves and converting said detected wave energy into at least one digital signal. A processor is configured to control said electronic pulser and receiver systems, to record said at least one digital signal, to extract at least one signal feature from said at least one digital signal, and to determine at least one characteristic of ice accreted on the outer surface of said probe.

In some embodiments, a method for the detection of ice accretion on aircraft and other engineered structures comprises generating a time-varying current with at least in at least one magnetostrictive coil in a probe to induce a time-varying magnetization in a ferromagnetic strip in the presence of a biasing magnetic field to generate shear horizontal-type guided waves in the body of said probe. The coil is positioned adjacent to said ferromagnetic strip. The guided waves are detected by at least one magnetostrictive coil in said probe. The guided waves are processed to extract at least one signal feature including at least one of optimum transmission frequency, wave packet arrival time, and wave attenuation. The at least one signal feature is correlated with the at least one characteristic of a layer of ice accreted on the outer surface of said probe.

BRIEF DESCRIPTION OF THE DRAWINGS

FIG. 12 is a conceptual illustration of one embodiment in which guided waves are propagated around the circumference of the probe body.

FIGS. 15a and 15b are diagrams of one embodiment of the ice sensing system.

DETAILED DESCRIPTION

This description of the exemplary embodiments is non-limiting and is intended to be read in connection with the accompanying drawings, which are to be considered part of the entire written description.

Figure 1:
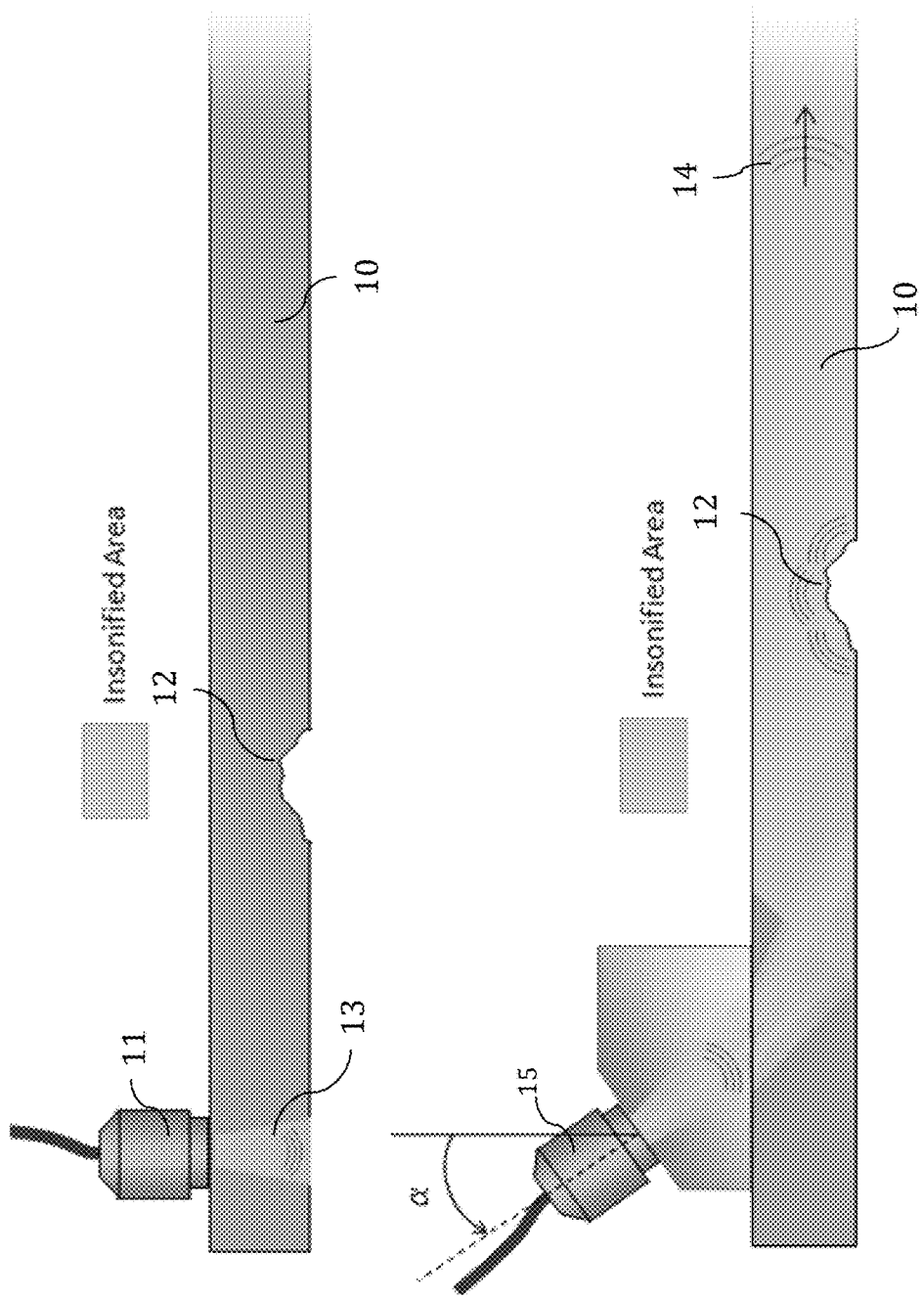
FIG. 1 is a comparison of ultrasonic bulk waves and ultrasonic guided waves.

Guided waves are elastic waves propagating in a bounded structure that is utilized as a waveguide to efficiently transmit one or more wave modes along the structure. Guided waves are formed from the constructive interference of ultrasonic bulk waves interacting with the boundaries of the waveguide structure in which they propagate. A conceptual illustration is provided in FIG. 1. In this illustration, an ultrasonic transducer 11 is generating bulk waves 13 in a structure 10. Alternatively, ultrasonic transducer 15 is generating guided waves 14 in structure 10 to remotely detect the corrosion defect 12. Guided waves are unique in the sense that they are capable of propagating for longer distances than traditional ultrasonic waves and can be used to inspect hidden/inaccessible structures like buried or cased piping and tubing. Unlike "spot-checking" with traditional ultrasonic techniques, guided waves provide a 100% or near 100% volumetric inspection. Furthermore, guided waves provide an efficient and cost-effective means of inspection due to increased inspection speed and simplicity. Ultrasonic guided waves have proven to be an excellent tool for the inspection of pipes, plates, and other structures for the detection of corrosion, cracks, and other instances of structural degradation. These characteristics of guided waves can also be employed for the detection of ice accretion on aircraft and other engineered structures.

One way in which ultrasonic guided waves are distinct from ultrasonic bulk waves is that, while bulk waves may exist in only three distinct modes, guided waves can exist in an infinite number of unique modes. Additionally, the wave velocity of these modes is dependent upon frequency, whereas bulk wave velocities are independent of frequency. This leads to complex wave mechanics behavior including phenomena such as wave dispersion, or the spreading of a wave packet as it travels. Dispersion occurs due to the variation of velocity as a function of frequency, and is related to another distinct characteristic of guided waves, which is that they exhibit two different velocities: phase velocity and group velocity. Phase velocity is the velocity of the phase (i.e. the peaks and valleys) of a single frequency component of the wave packet, and group velocity is the velocity of the energy (i.e. the wave packet as a whole).

Figure 2A:
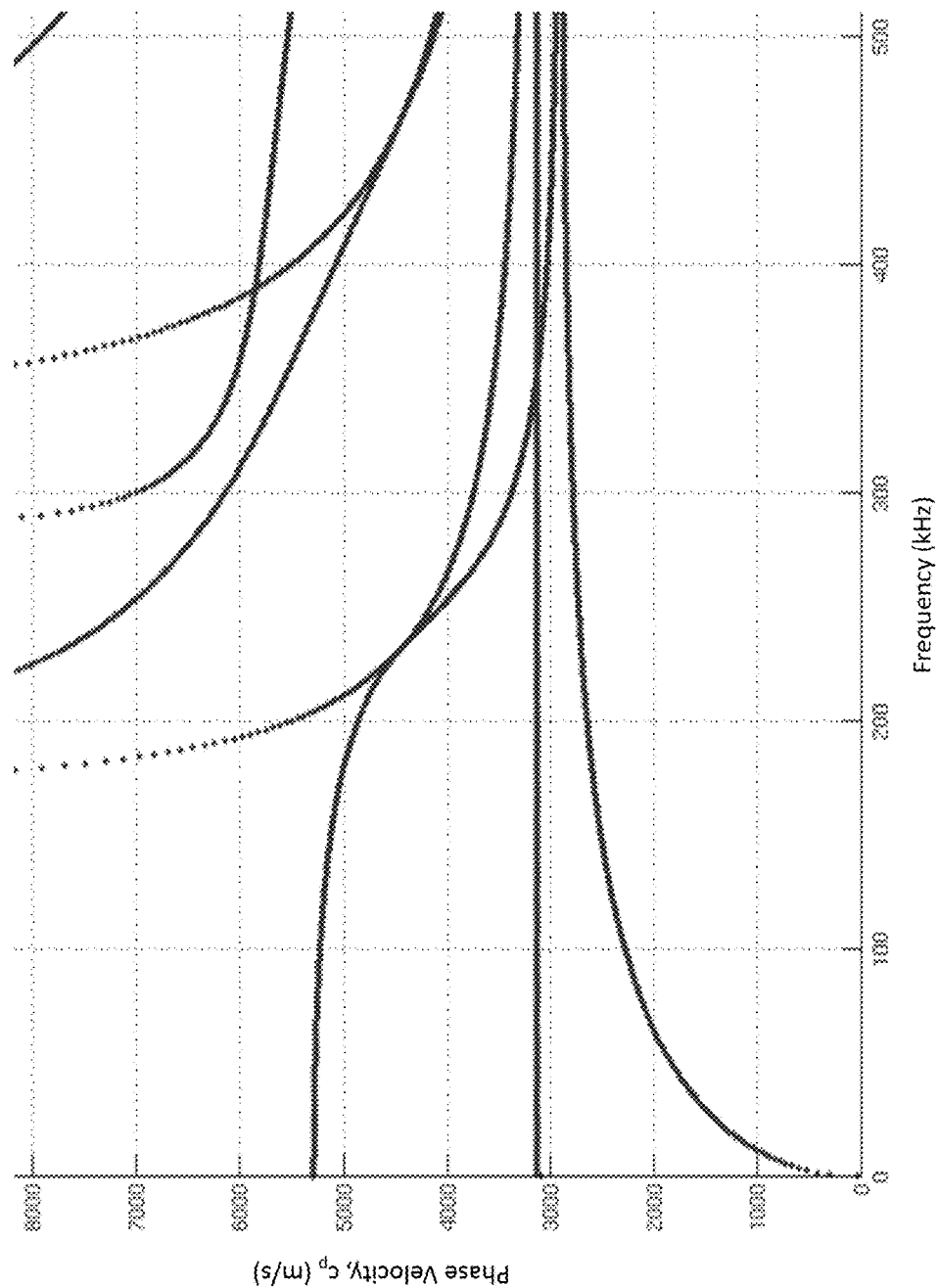
FIGS. 2a and 2b illustrate guided wave phase velocity and group velocity dispersion curves, respectively.
Figure 2B:
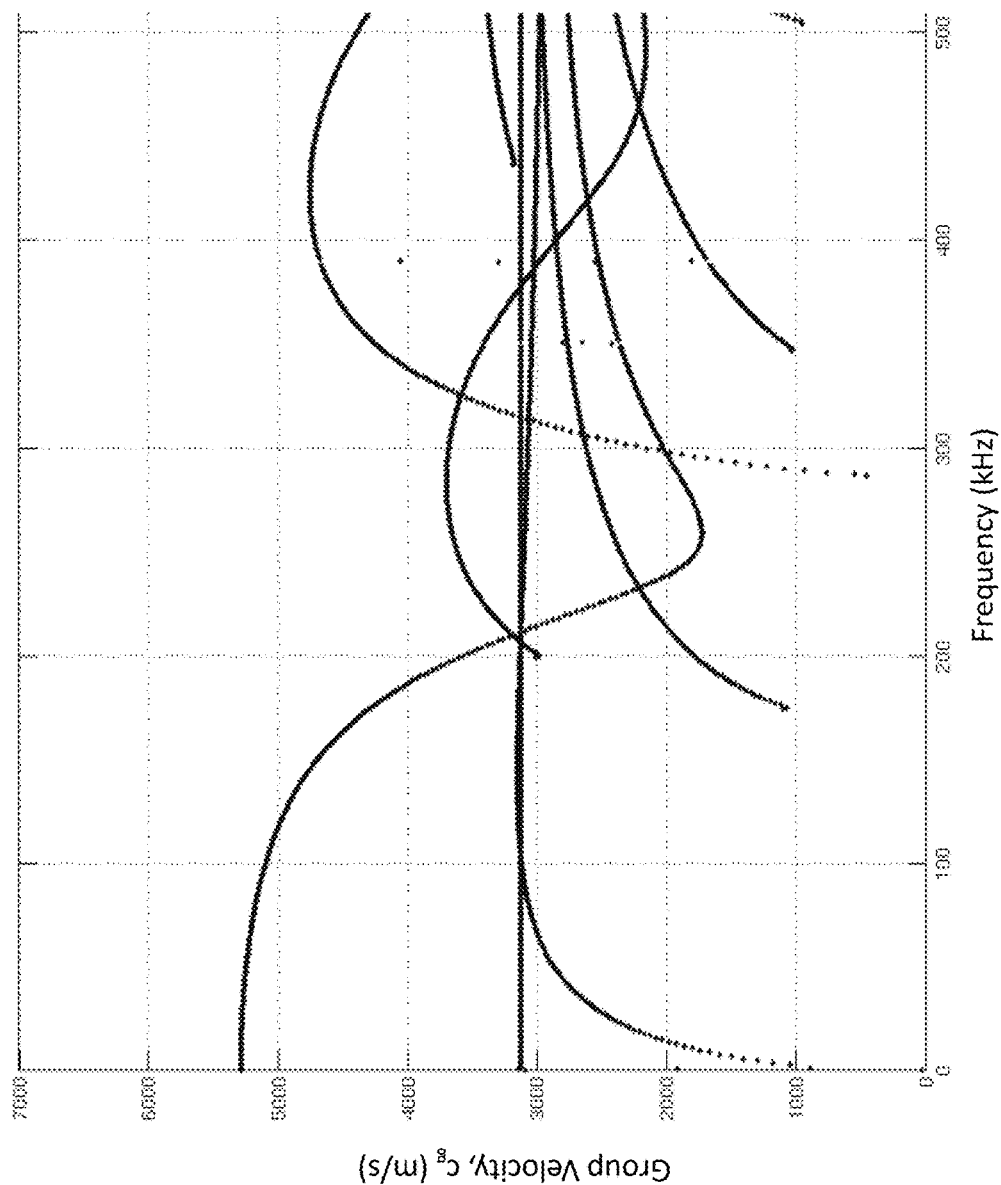

Dispersion curves are used to describe the complex relationship between wave mode, wave velocity, and frequency that exists for guided waves in a particular structure. One example of a phase velocity dispersion curve for the guided wave modes at frequencies up to 500 kHz in a ⅜"-thick aluminum plate is provided in FIG. 2a; note that multiple modes exist, particularly at higher frequencies, and that the velocity of these modes is dependent on frequency. The group velocity curves for this same structure are provided in FIG. 2b.

The dispersion curves are unique to the structure for which they were derived. Changes in material properties, changes in waveguide cross-section, or the addition of another layer of material to the waveguide would alter these dispersion curves. This is the fundamental principle of which the disclosed systems and methods take advantage to detect ice accretion. Even a very thin ice layer added to a properly-designed waveguide can alter the characteristics of the dispersion curve, and these changes can be detected in a number of ways with a properly designed sensor and algorithm.

Figure 3A:
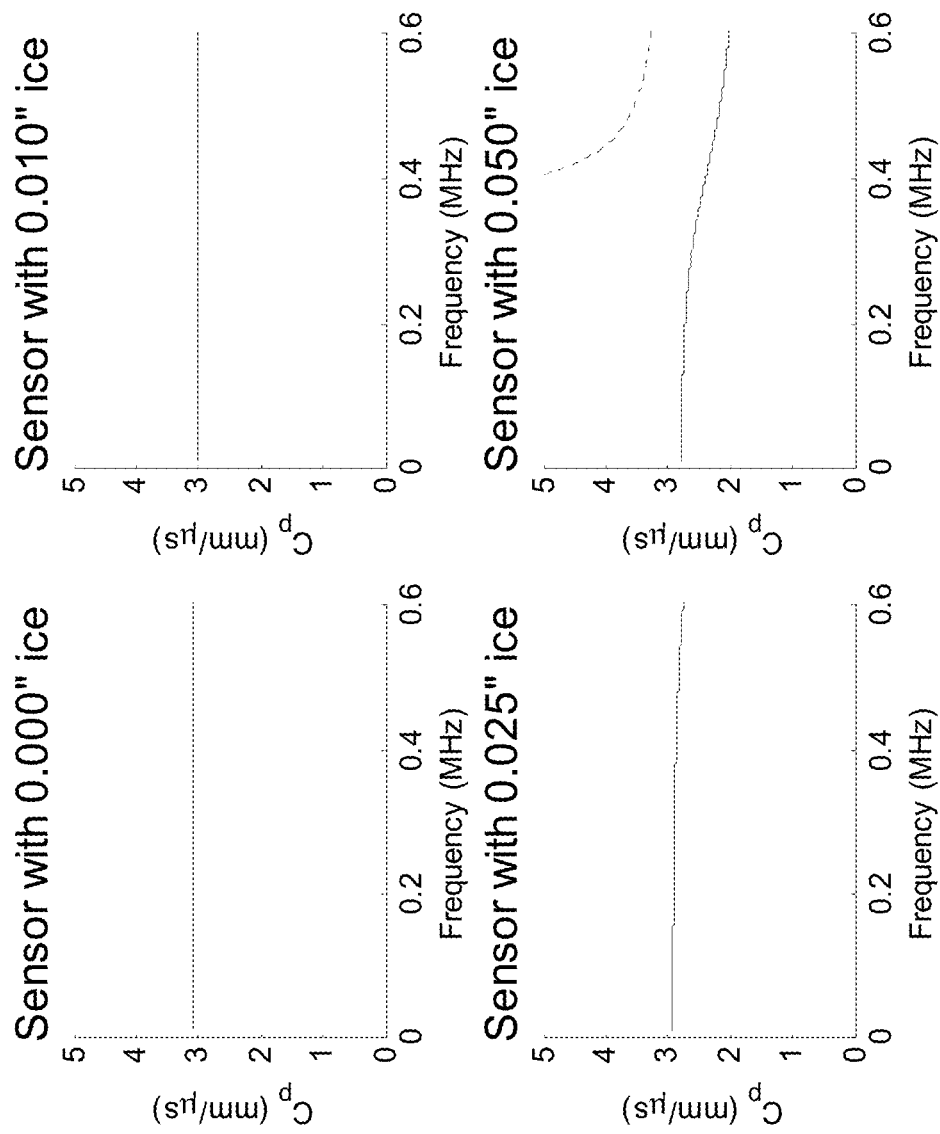
FIGS. 3a and 3b illustrate the changes in phase velocity and group velocity dispersion curves, respectively, of a magnesium probe body as ice is accreted on its surface.
Figure 3B:
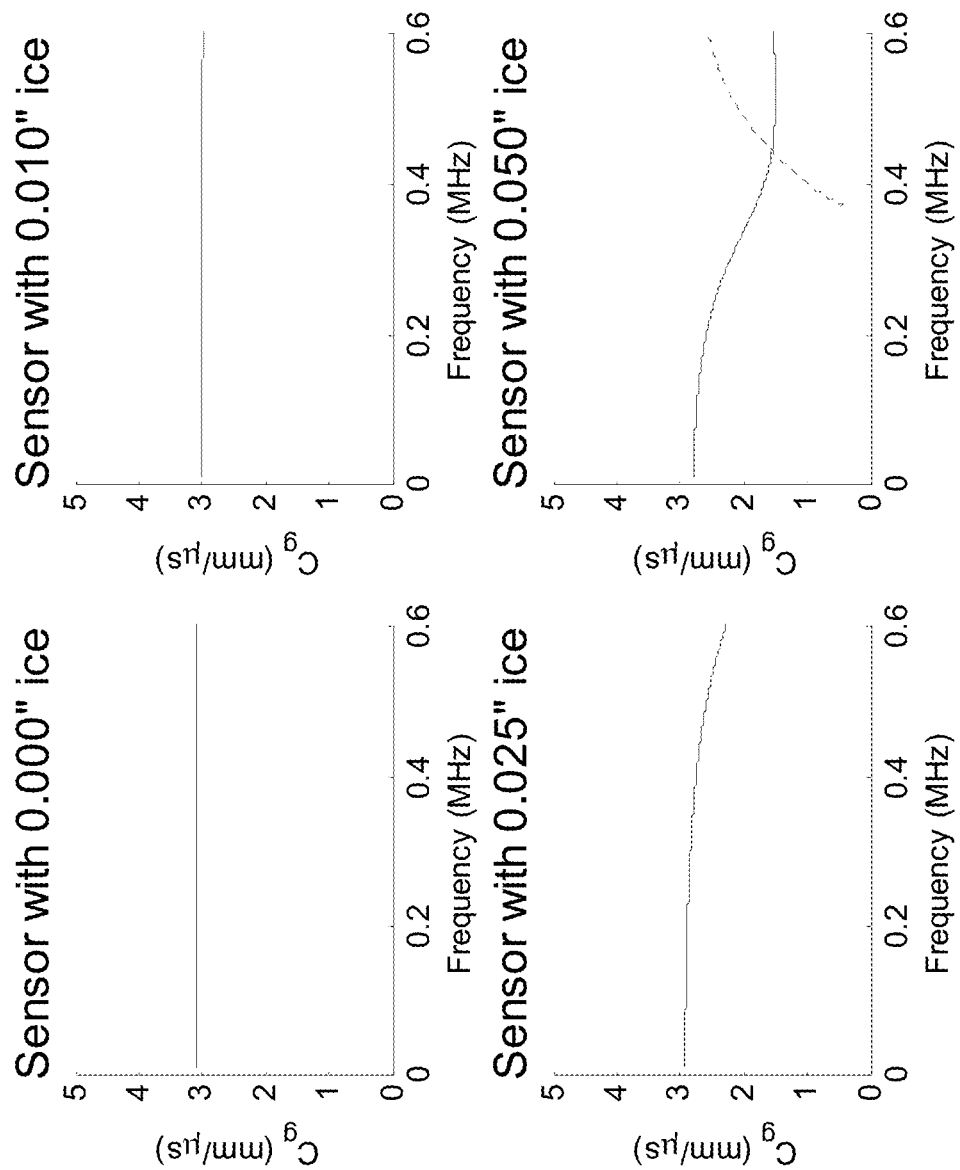

FIG. 3a illustrates one example of the effect of ice accretion on one embodiment of a magnesium ice sensor probe body. Note that the shear horizontal guided wave mode line shifts increasingly downward in phase velocity and changes shape as more ice is accreted on said sensor. FIG. 3b illustrates the similar effects on the group velocity of the same guided wave mode.

The disclosed systems and methods utilize only the shear horizontal-type guided wave modes in the probe body skin (i.e. the waveguide), which are the modes that feature predominantly in-plane shear strains perpendicular to the wave propagation direction. The primary advantage of this type of mode is that it is highly insensitive to liquid loading on the surface, which means that its properties will be unaffected by the presence of rain, glycol, or other fluids on the surface of the probe; this is due to the fact that shear energy is not supported by inviscid fluids. Additional advantages of the shear-horizontal modes include the presence of fewer guided wave modes on the dispersion curves and the potential for excellent excitability, mode control, and signal-to-noise ratio with magnetostrictive transducers, which provide their own advantages.

The disclosed systems and methods include a probe body, at least one magnetostrictive guided wave sensor, a means for generating an alternating current in at least one sensor coil to generate ultrasonic shear horizontal-type guided waves in said probe body, a means of detecting said guided waves after they have propagated through the probe body over some distance, a means of converting said detected wave energy into a digital signal, a processor to extract signal features from the digital signal and determine at least one of the presence and severity of ice accretion, and a non-transitory memory storage medium. In some embodiments, the at least one magnetostrictive guided wave sensor includes a ferromagnetic strip coupled to the inner surface of said probe body, at least one sensor coil, and at least one biasing magnet.

Figure 4A:
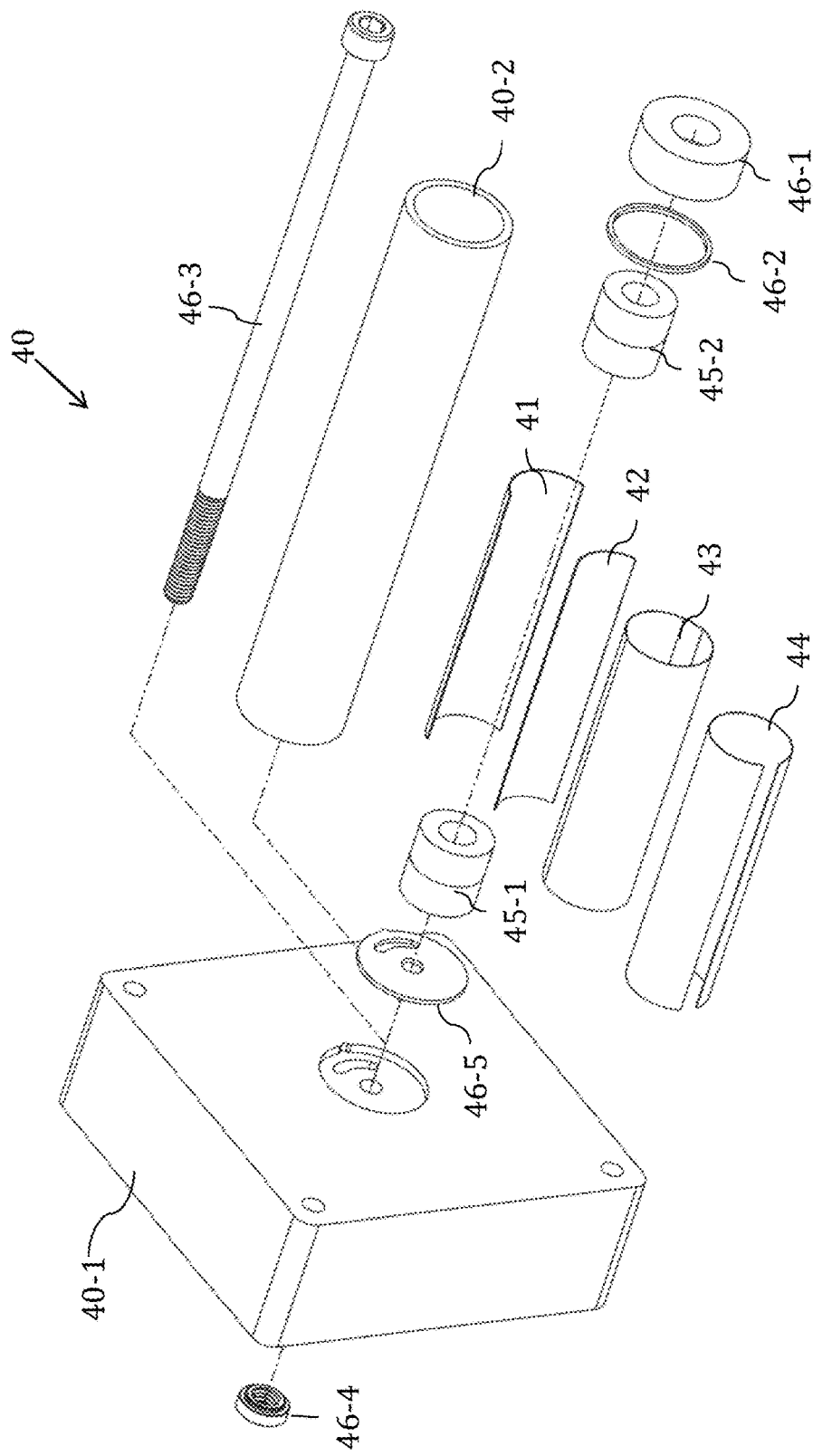
FIG. 4a is an exploded view of one embodiment of the ice sensing probe.

FIG. 4a is an exploded view diagram of one embodiment of an ice sensor probe in accordance with some embodiments. As shown in FIG. 4a, ice sensor probe 40 includes probe base 40-1 and aerodynamic probe body section 40-2, which acts as the waveguide in which the guided waves can propagate. Said probe 40 further comprises ferromagnetic strip 41, at least one flexible magnetostrictive sensor coil 42, a low-friction PTFE decoupling layer 43, and at least one permanent magnet 45-1 and 45-2, as well as a flexible heater coil element 44. In some embodiments, the probe body 40-2 is sealed by means of a central bolt 46-3 that compresses gasket 46-2 between probe body 40-2 and end cap 46-1. Additional elements include threaded nut 46-4 and lower gasket 46-5. Central bolt 46-3 is sized and configured to be received through probe body section 40-2, end cap 46-1, gasket 46-2, the at least one permanent magnets 45-1, 45-2, coil 42, decoupling layer 43, and heater element 44, and lower gasket 46-5 to secure these elements to probe body 40-1 by engaging threaded nut 46-4.

Figure 4B:
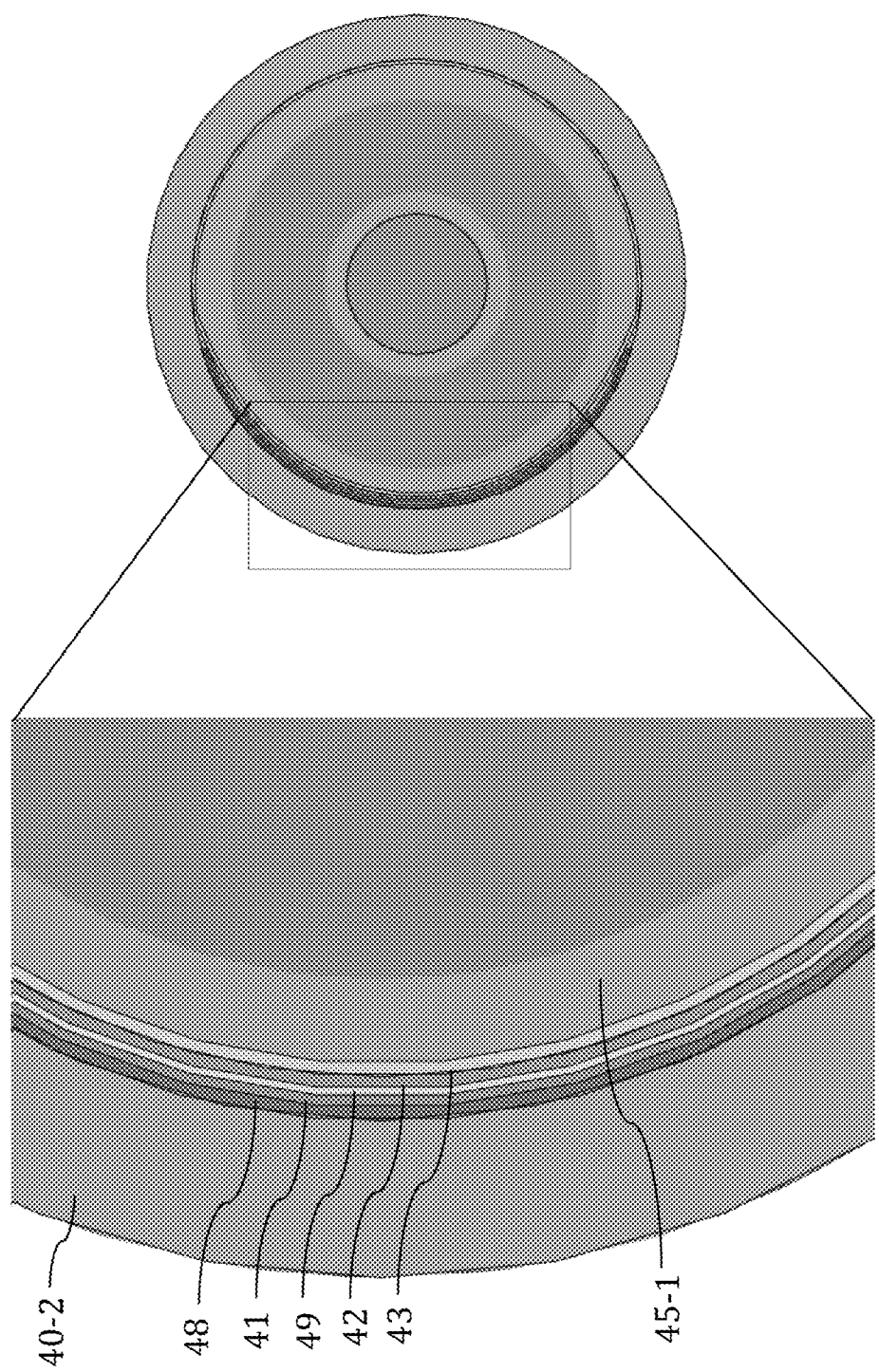
FIG. 4b is a cross-sectional view of one embodiment of the ice sensing probe.

FIG. 4b is a cross-sectional diagram of one example of the ice sensor probe in accordance with some embodiments. FIG. 4b shows the relative position of components including probe body 40-2, ferromagnetic strip 41, which is coupled to said probe body 40-2 by means of bonding layer 48, sensor coil 42, which is bonded to said ferromagnetic strip by means of bonding layer 49, decoupling layer 43, and biasing magnet 45-1.

Figure 5:
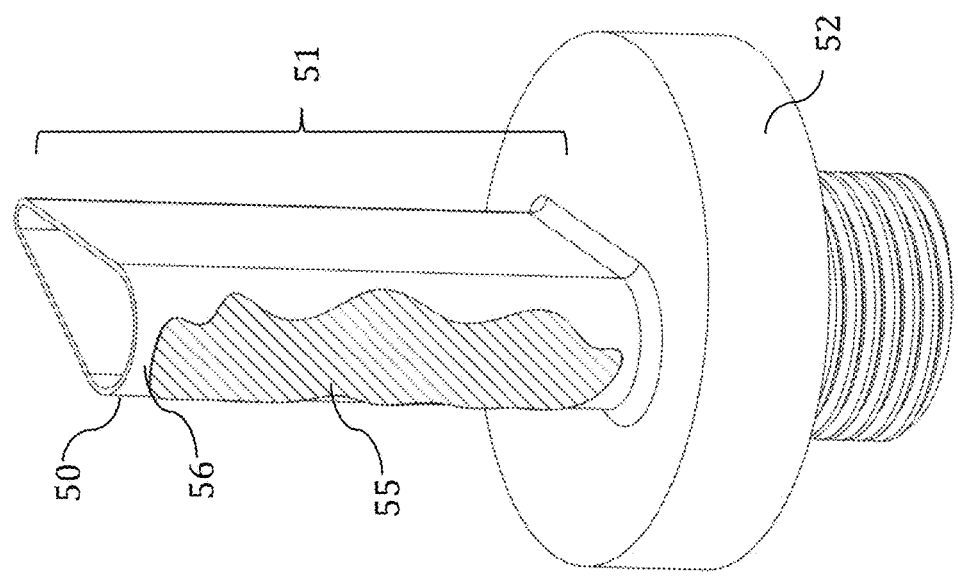
FIG. 5 is an illustration of one embodiment of the ice sensing probe with ice accreted on its outer surface.
Figure 6B:
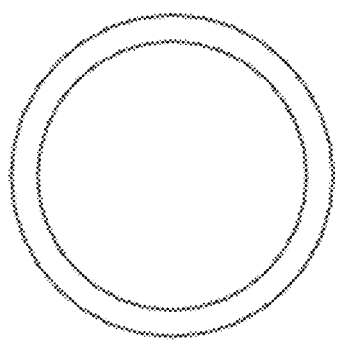
FIGS. 6a through 6d illustrate various embodiments of the ice sensing probe body cross-section.
Figure 6D:
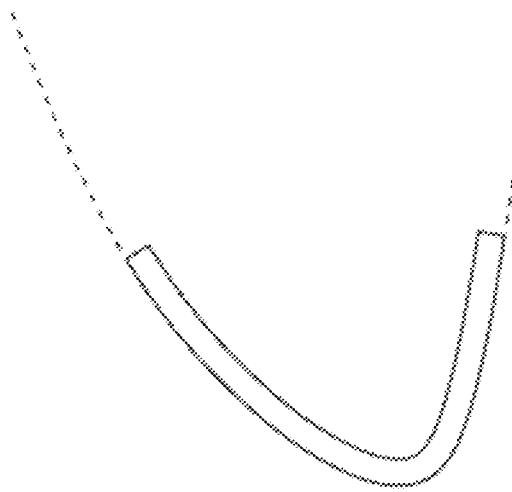
Figure 6A:
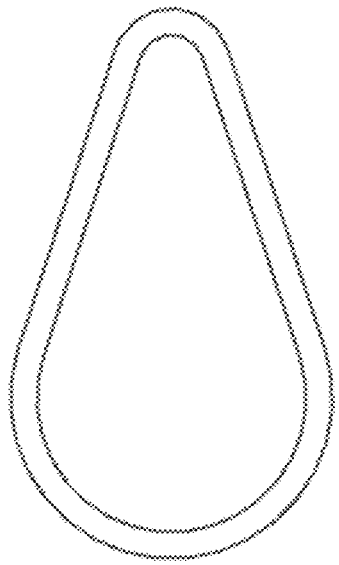
Figure 6C:
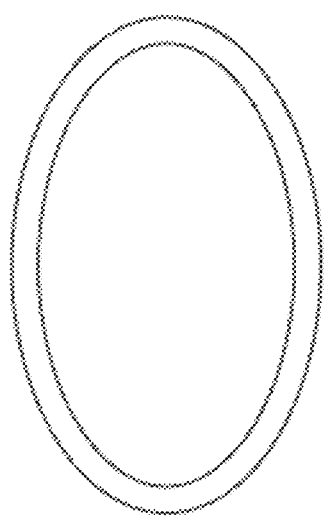

The probe body 50, as shown in FIG. 5 with accreted ice 55, includes an aerodynamic section 51, which is exposed to icing conditions, and a base 52, which is used to connect the probe to the structure via a threaded, clamped, bolted, or other mechanism as will be understood by a person of ordinary skill in the art. In various embodiments, the aerodynamic section 51 may have an airfoil-shaped cross-section (FIG. 6a), a circular cross-section (FIG. 6b), an elliptical cross-section (FIG. 6c), or a simple or compound curved cross-section (FIG. 6d) that allows air to flow over the outer skin of said section in a manner that allows for efficient ice accretion. The leading edge 56 of said aerodynamic section 51, i.e. the side that is exposed to icing conditions, features a thin skin upon which the ice accretion is detected by ultrasonic guided wave means.

In some embodiments, a heater element 44 is also integrated into the probe to rapidly melt or ablate ice from the surface of the probe leading ice as soon as ice accretion is detected. This allows the system to detect ice, clean the surface of the probe of that ice, and subsequently detect ice again as more accretes on the clean surface. In some embodiments, ice accretion rate can be approximated by the frequency with which the accretion-melt cycle occurs.

Figure 7A:
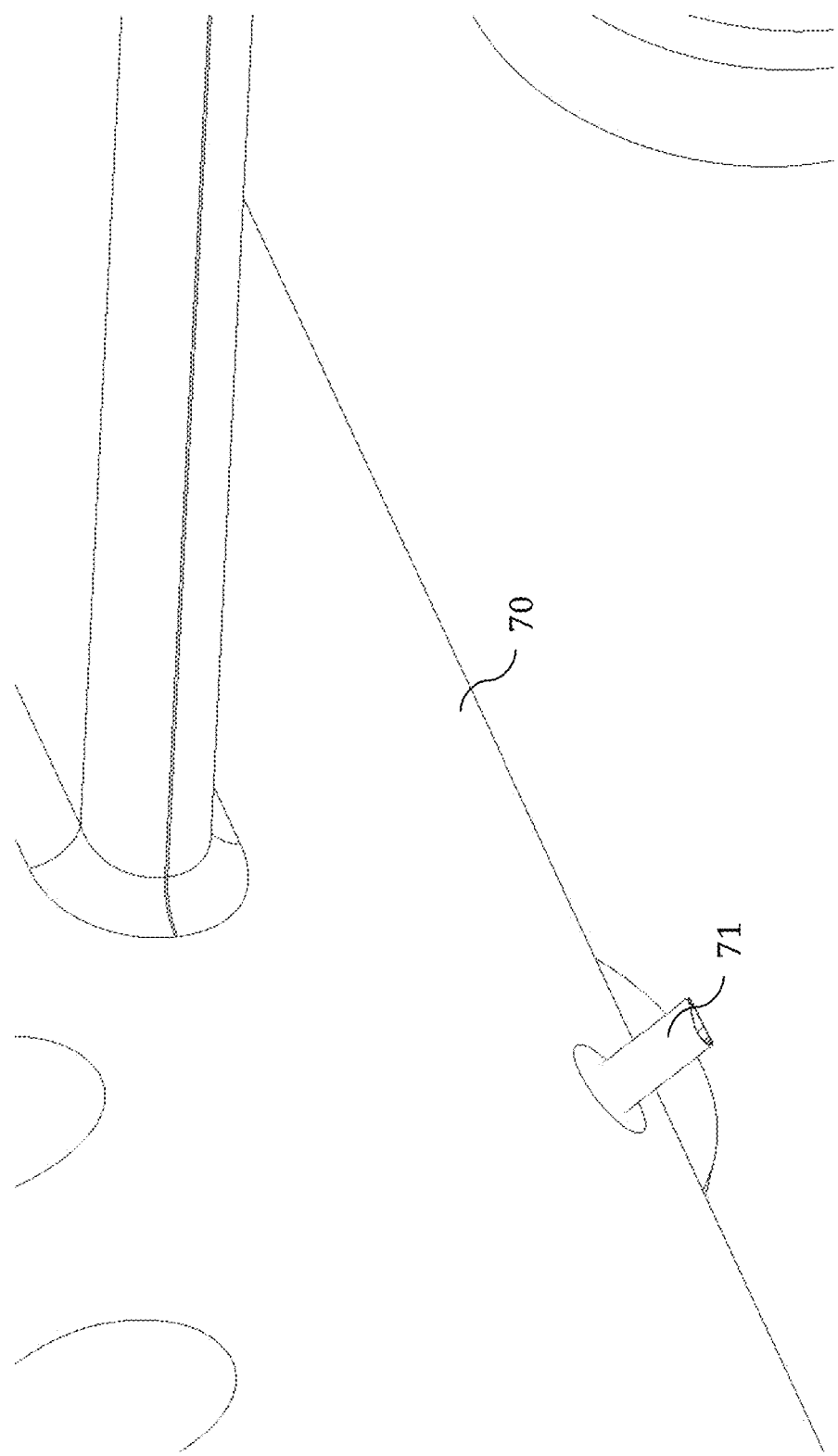
FIG. 7a is a conceptual illustration of an embodiment in which the ice sensing probe is mounted externally to a structure that may experience ice accretion.

In reference, to FIG. 7a, the ice sensing probe 71 may be installed on an aircraft 70 or another engineered structures for which ice sensing is desired. The probe 70 illustrated in FIG. 71 can be installed on the structure so that the outer surface of the probe skin is exposed to icing conditions. As ice accretes on the outer surface of the probe, ultrasonic shear horizontal waves are transmitted and received through the probe skin to detect ice accretion on said surface. The guided wave sensors are housed within the probe and coupled to the inner surface of the probe skin. The ice sensing probe has been demonstrated to have sensitivity to ice accretion as thin as 0.005".

Figure 7B:
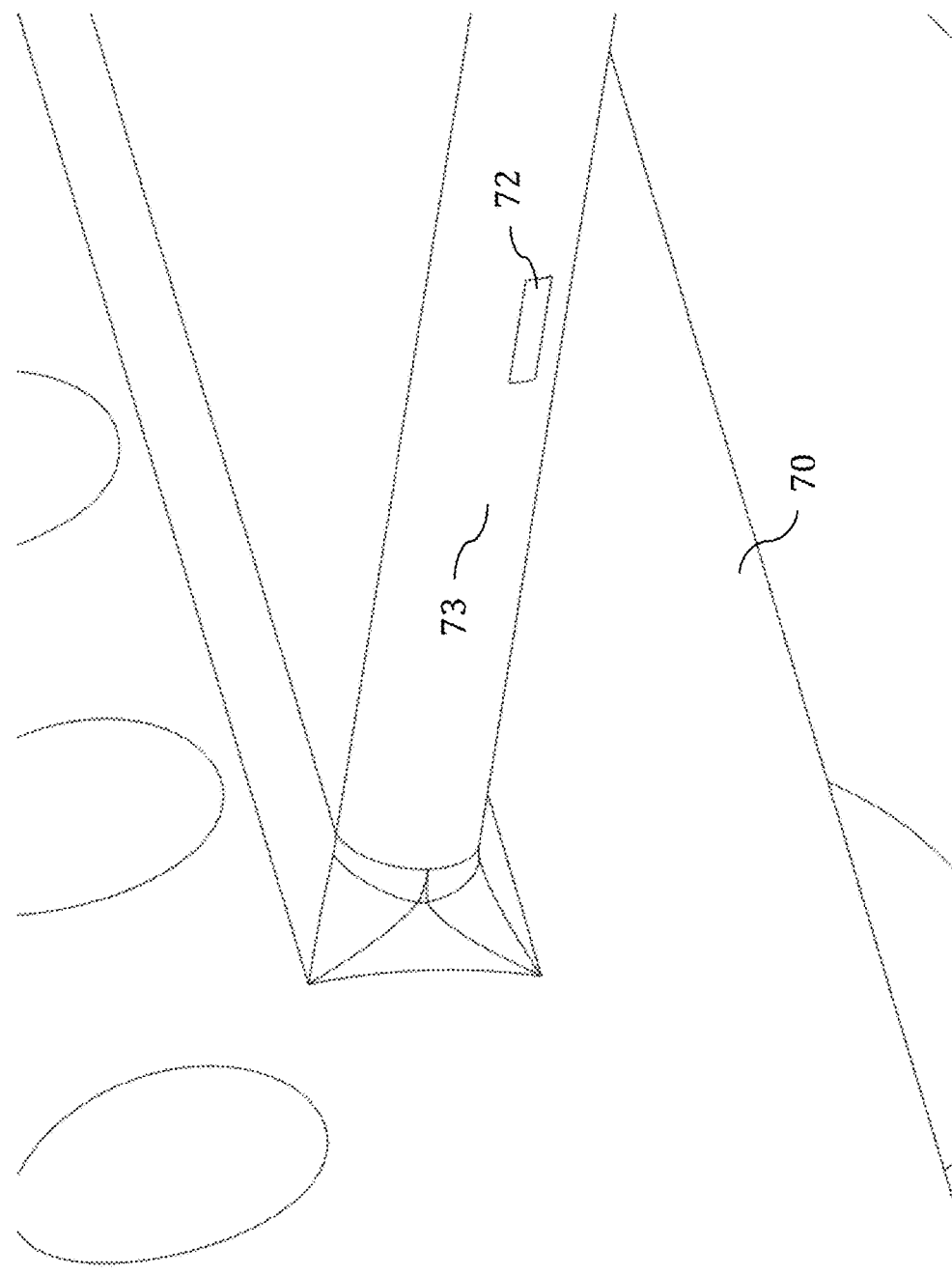
FIG. 7b is a conceptual illustration of an embodiment in which the ice sensing probe is mounted flush to a structure that may experience ice accretion.

In some embodiments, as illustrated in FIG. 7b, the probe skin 72 is mounted flush with or is comprised of a component 73 of said engineered structure 70 such that the ice sensing probe is contained entirely, or at least partially, within said structure.

In some embodiments, the leading edge assembly, which includes the thin skin sensing surface, and the guided wave sensors, is removable from the probe body. In other embodiments, the leading edge is a permanent component of the probe body.

Various means of guided wave transduction exist including piezoelectric transducers, electromagnetic acoustic transducers (EMATs), impact devices, and magnetostrictive transducers. Magnetostrictive transducers have been utilized for the purposes of ultrasonic guided wave generation since the 1970s. In some embodiments, magnetostrictive transducers are utilized because of their low profile, low weight, low cost, high signal-to-noise ratio, flexibility, ruggedness, efficient excitation of shear horizontal guided wave modes, and excellent guided wave mode control. The low-profile, lightweight, flexible nature of the magnetostrictive transducers makes them excellent candidates for aerospace applications and allows them to be integrated into a small probe that may have a small radius of curvature on the ice-exposed surface. The excellent mode control, wave generation efficiency, and high signal-to-noise ratio also make the magnetostrictive sensors superior to EMATs and piezoelectric transducers for this application, which is important for accurately and robustly monitoring for the accretion of very thin, yet highly critical, layers of ice. However, EMATs and piezoelectric transducers can be implemented in some embodiments.

Figure 8:
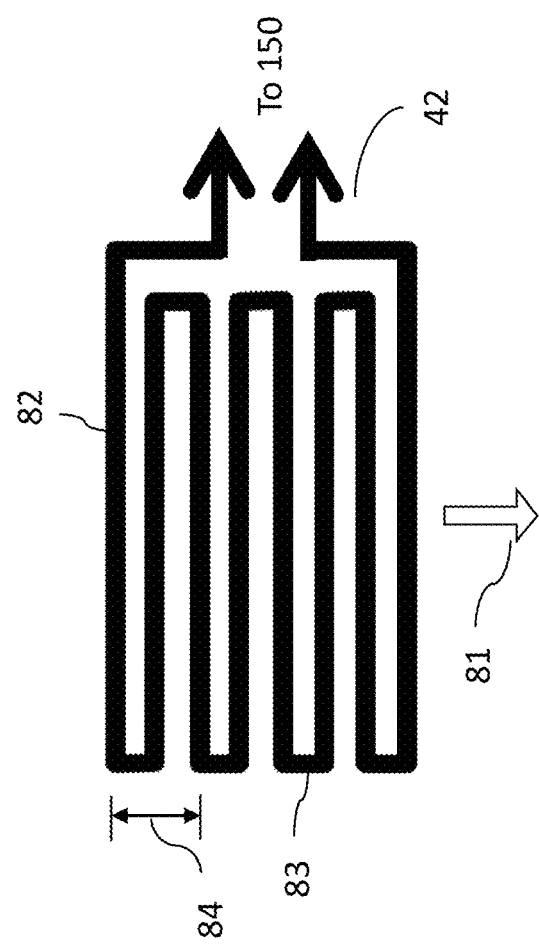
FIG. 8 is a conceptual illustration of a magnetostrictive sensor coil.

In some embodiments, a probe sensor coil 42 generates guided waves via the Joule magnetostrictive effect by which a time-varying strain is induced in the magnetostrictive material by means of generating a time-varying current in the probe coil in the presence of a biasing magnetic field that is perpendicular to the direction of wave propagation. Turning now to FIG. 8, the active portions 82 of the traces of the coil 42 are oriented perpendicular to the wave propagation direction 81 and parallel to the biasing magnetic field and the surface of the probe body such that they induce a time-varying magnetic field in the ferromagnetic material that is parallel to the wave propagation direction. By this process, shear horizontal-type guided waves are generated in the ferromagnetic material and the structure to which the ferromagnetic material is coupled. By the inverse Villari effect, incident shear horizontal-type guided waves are detected by the probe.

In some embodiments, the ferromagnetic material is an iron cobalt alloy. In other embodiments, said ferromagnetic material may be iron cobalt, nickel, Metglas, or other materials selected from the set of well-known ferromagnetic materials.

In some embodiments, the biasing magnetic field is established by means of at least one permanent magnet within the probe body. In additional embodiments, the biasing magnetic field is established by means of an electromagnet.

In some embodiments of a sensor coil, the at least one probe coil includes a flexible printed circuit board (PCB) with coil traces predisposed to generating a shear-horizontal guided wave having a predetermined wavelength. Said at least one coil is bonded or held in a fixture so that it is held in close proximity to said ferromagnetic material, which is coupled to the inner surface of the probe skin.

As shown in FIG. 8, a meandering trace can be provided on a dual-layer coil such that the trace fingers 83 are separated by a distance 84. In some embodiments, the distance 84 is equal to one half of the intended wavelength of the guided waves. The wavelength, and thus the spacing of the coil fingers 83, is predominantly determined by the thickness and the material properties of the skin structure in order to optimize the algorithm for maximum ice accretion sensitivity while maintaining a reasonable degree of linearity to thicker layers of ice. Shorter wavelength coils may be more sensitive to thinner layers of ice, but the presence of multiple modes and more complex wave propagation phenomena will occur if the ice becomes too thick. Therefore, coil spacing is selected so that the system functions robustly over the desired range of ice thickness values.

Figure 9:
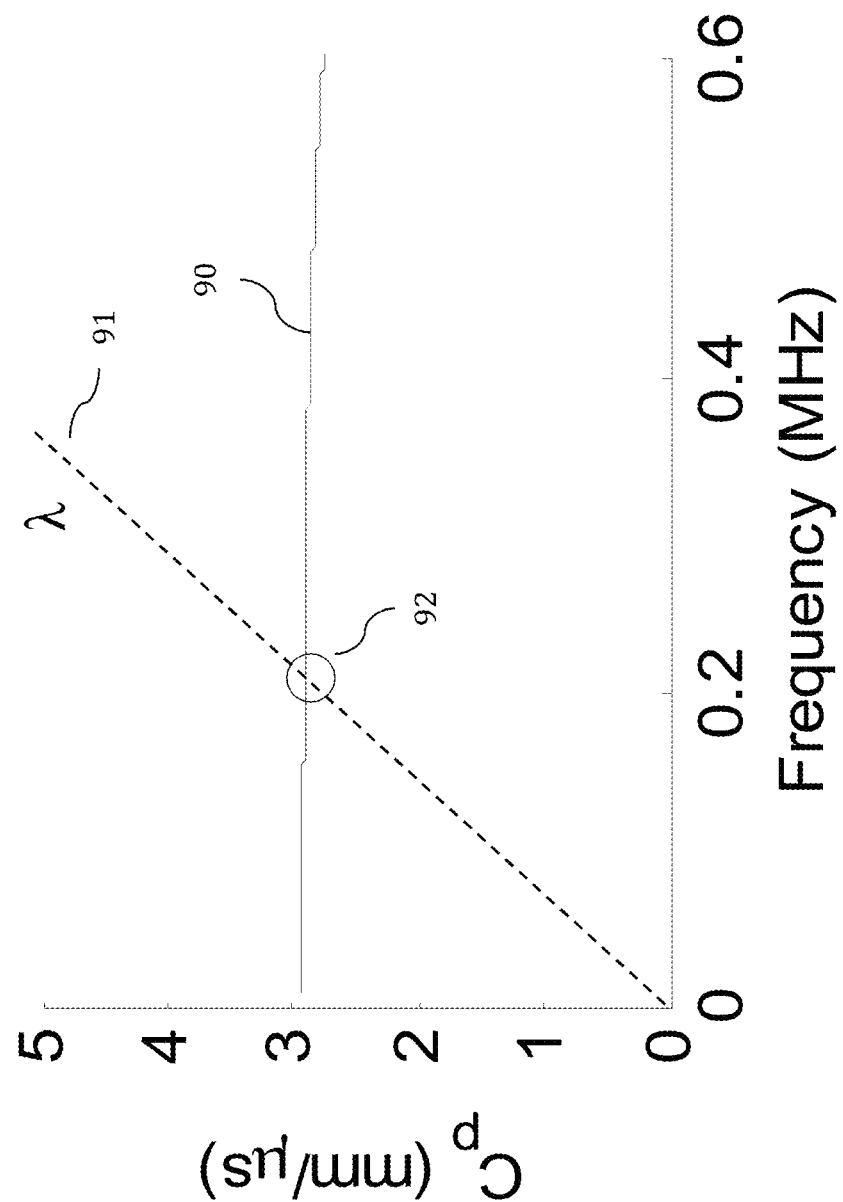
FIG. 9 is a dispersion curve with a superimposed line of constant wavelength.

This type of transducer has a fixed wavelength, and thus regardless of the structure to which it is applied, it will preferentially generate and detect guided waves having said predetermined wavelength. Referring to FIG. 9, this constant wavelength can be represented on a phase velocity dispersion curve by a sloped line 91, since the wavelength λ of a guided wave is related to the frequency f and phase velocity $c_p$ according to equation (1).

$$\lambda = \frac{c_p}{f} \quad (1)$$

Because of the constant-wavelength nature of said transducer design, the optimum guided wave excitation and detection will occur at the frequency point 92 at which this constant-wavelength line 91 crosses the shear-horizontal guided wave mode line 90 on the phase velocity dispersion curve. In the example shown in FIG. 9, the optimum transmission frequency occurs at 200 kHz. As ice accretes on the opposite surface of the skin structure, the phase velocity dispersion curves will shift and change shape, as illustrated in FIG. 3a, and the optimum transmission frequency will shift. An ice sensing algorithm can be utilized to detect the shifts in said dispersion curves and thus detect the accretion of ice on the probe.

Figure 10B:
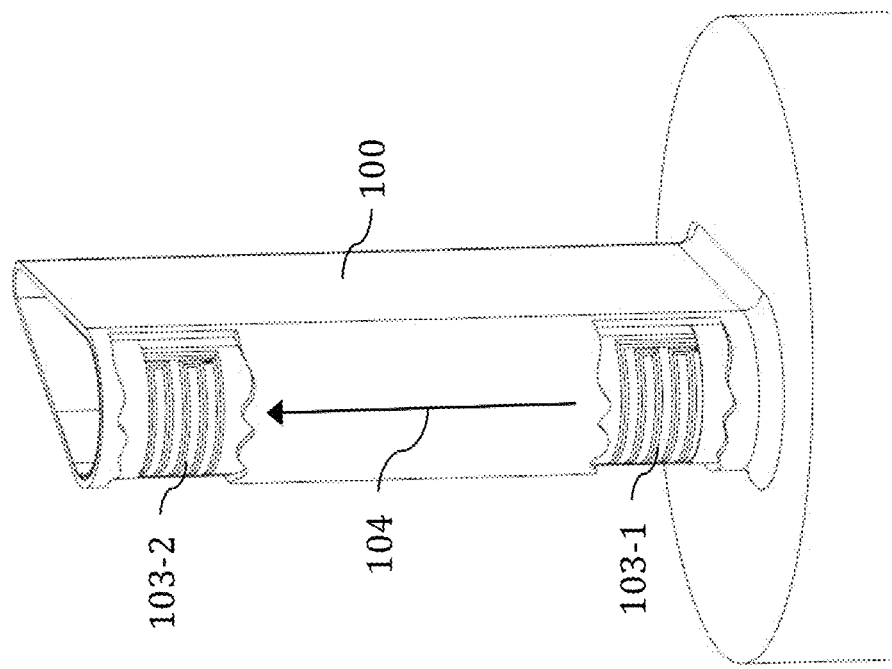
FIGS. 10a and 10b are conceptual illustrations of embodiments featuring pulse-echo and pitch-catch sensor coil configurations, respectively.
Figure 10A:
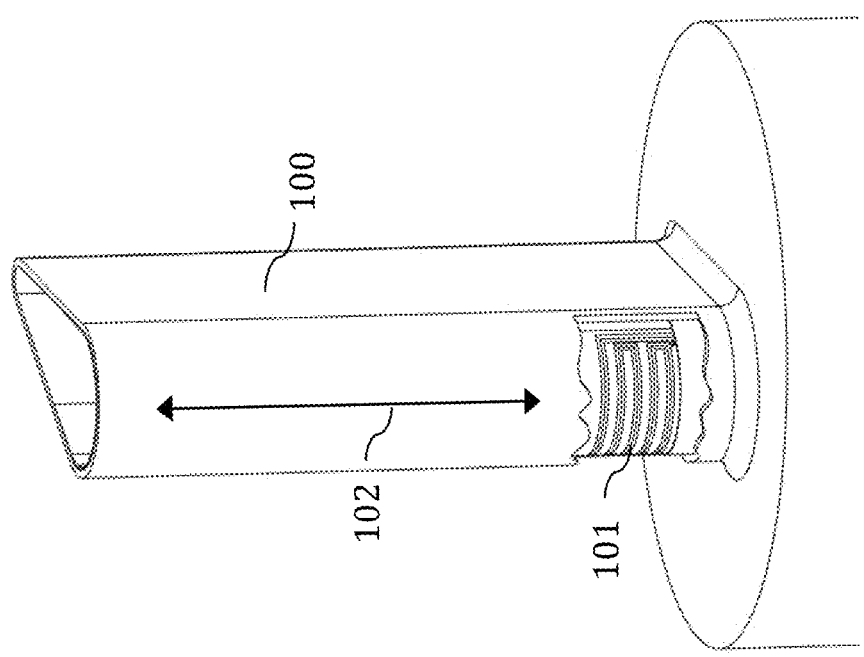

In some embodiments, as illustrated in FIG. 10a, a magnetostrictive probe 100 is configured such that at least one coil element 101 generates outgoing guided waves 102 and subsequently detects guided wave signals in a "pulse-echo" configuration. In alternative embodiments, as illustrated in FIG. 10b, a magnetostrictive probe 100 is configured such that at least one coil element 103-1 generates the outgoing guided waves 104 and at least one additional coil element 103-2 detects guided wave signals in a "pitch-catch" configuration.

Figure 11B:
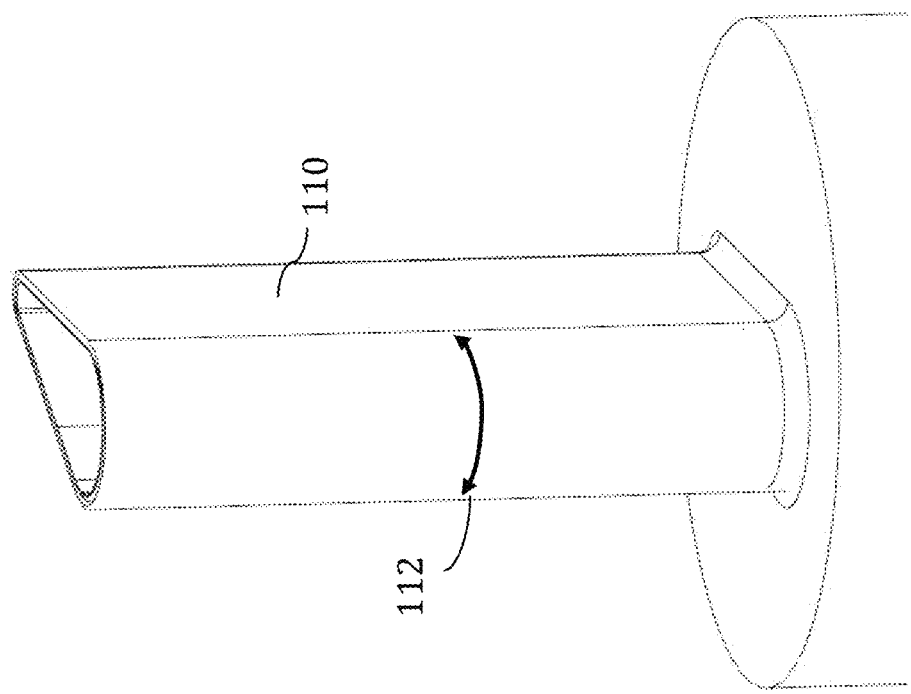
FIGS. 11a and 11b are conceptual illustrations of embodiments in which guided waves are propagated and reflected longitudinally and laterally, respectively, along the probe body.
Figure 11A:
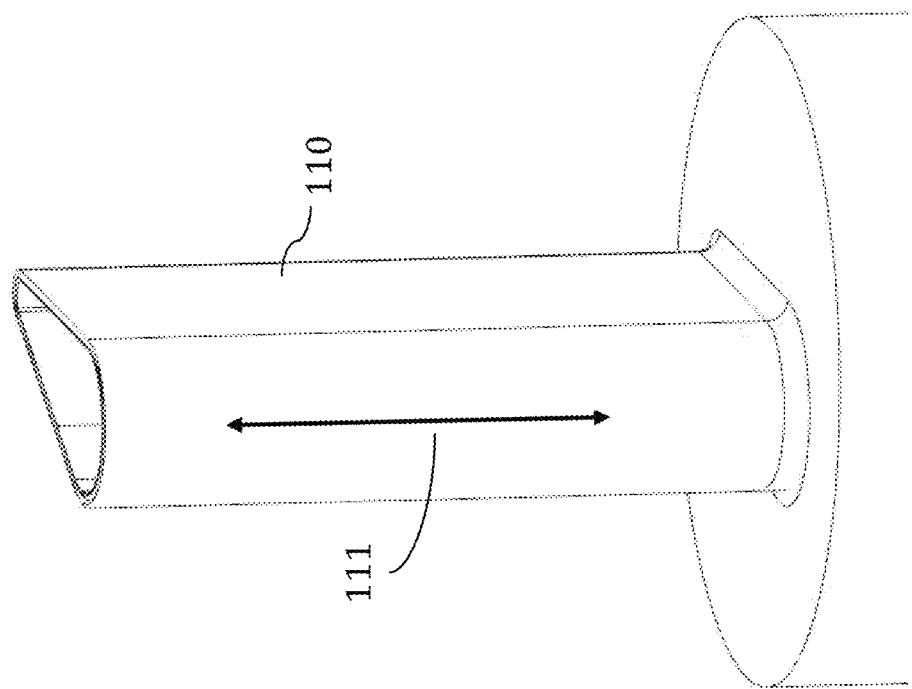

In some embodiments, as illustrated in FIG. 11a, the wave propagation direction is longitudinal as shown by arrow 111, i.e. along the greater dimension of the probe body 110, in either a pulse-echo or pitch-catch configuration. In some embodiments, as illustrated in FIG. 11b, the wave propagation direction is lateral as shown by arrow 112, i.e. along the shorter dimension of the probe body 110, in either a pulse-echo or pitch-catch configuration. When the propagation direction is either longitudinal or lateral embodiments, the ice sensing region is limited to the region of the probe body between the sensor coils or sensor and reflector.

FIG. 12 illustrates one example of a probe in which the wave propagation occurs in a complete path 121 around the circumference of the probe body 120. The probe 120 can be configured to provide the circumferential wave propagation direction in either a pulse-echo or pitch-catch configuration. In said embodiments, the ice sensing region includes the full circumference of the probe within the axial region defined by the at least one sensor coil. One advantage of said circumferential embodiments is that for applications in which ice accretion may occur from multiple directions, e.g. on a helicopter, bridge, or wind turbine tower, a single guided wave ice sensor can detect said icing independent of ice impingement direction.

The material of which the probe skin may be selected from the family of metals or from the family of composite materials. The primary factors in selecting a probe skin material include low material density, low ultrasonic shear wave attenuation, high material strength, high a degree durability, a low coefficient of thermal expansion, and resistance to corrosion, moisture, and degradation. Guided wave dispersion curve analysis shows that a probe skin material with low density, more specifically a density close to that of water ice, provides maximum sensitivity to thin ice accretion. In some embodiments, the probe skin includes a magnesium alloy or a quasi-isotropic carbon fiber-reinforced polymer material.

As with all guided wave applications in composite materials, the anisotropy of the material can affect the wave propagation characteristics of the waves, which generally are dependent on wave propagation direction relative to the material orientation. Many engineered composite skin structures are quasi-isotropic, meaning that they have plies or woven layers laminated in a variety of direction. In such cases, the propagation direction of the guided waves is less critical. In some embodiments, however, the sensor(s) are aligned such that the wave propagation path is aligned with a fundamental direction in the material. Therefore quasi-isotropic or unidirectional composite materials are preferable in embodiments in which a probe body is comprised of a composite material.

The thickness of the probe body skin also is taken into account in order to achieve the maximum sensitivity to thin ice layer accretion while maintaining robustness across a range of accreted ice thicknesses. Additionally, the wavelength of the magnetostrictive sensor coil with respect to the probe skin thickness is taken into account, as the dispersion curves for guided waves in plate-like structures are dependent on the ratio of the guided wave wavelength to the thickness of the plate-like waveguide structure.

In some embodiments, the probe body includes a magnesium alloy tube having a wall thickness between 0.045" and 0.065" and an outer diameter between 0.50" and 0.75", and the magnetostrictive sensor coil is designed to preferentially excite shear horizontal guided waves having a wavelength between 12 and 16 mm. However, a person of ordinary skill in the art will understand that such materials, sizes, and arrangements are not limiting and that other materials, sizes, and arrangements may be implemented.

In some embodiments, a multi-frequency guided wave signal analysis approach, in which guided wave data is transmitted through the skin structure over a predetermined range of frequencies to identify the presence of accreted ice, is implemented. In some embodiments, this multi-frequency data is acquired by applying a transient, broadband pulse to the sender coil and decomposing the received data into the frequency domain. This can be accomplished by using a fast frequency analysis (FFA) approach, in which tone burst signals having several cycles at one center frequency are applied to the sensor coil, the corresponding signal data is recorded, and this process is repeated over a predetermined range of center frequencies at a predetermined increment.

Figure 13A:
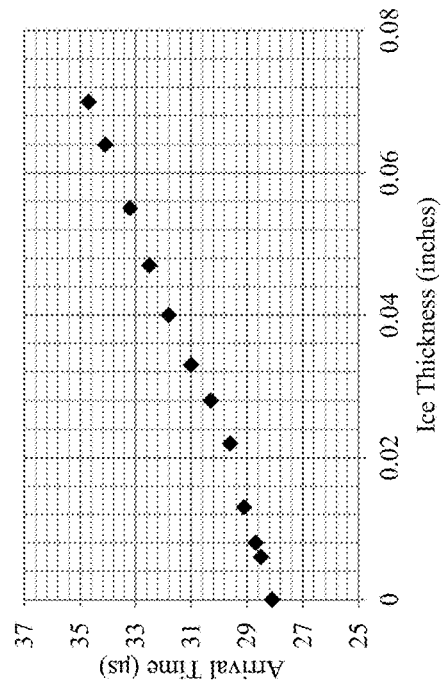
FIG. 13a illustrates the relationship between the optimum transmission frequency feature value and accreted ice thickness for one embodiment of the ice sensing system.

Referring again to FIG. 3a, shifts in the phase velocity dispersion curves are indicative of ice accretion, which manifests as shifts in the optimum transmission frequency of guided waves since the wavelength is fixed as demonstrated above in equation (1). FIG. 13a illustrates one example of the relationship between optimum transmission frequency and accreted ice thickness during a typical test.

In some embodiments, one of the signal features utilized for ice detection is the optimum transmission frequency of guided waves propagating through the probe skin.

Figure 13B:
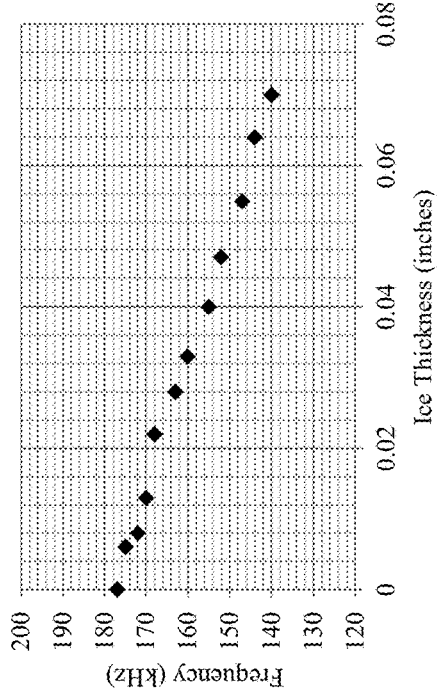
FIG. 13b illustrates the relationship between the wave packet arrival time feature value and accreted ice thickness for one embodiment of the ice sensing system.

Another effect of ice accretion on the structure is a shift in arrival time of the guided wave packet. Since the wave propagation distance in the probe skin remains constant for all intents and purposes, shifts in arrival time are primarily due to changes in the group velocity of the guided waves propagating in the probe skin. As illustrated in FIG. 3b, shifts in the group velocity dispersion curves are also indicative of ice accretion. FIG. 13b illustrates the relationship between wave packet arrival time and accreted ice thickness during a typical test.

In some embodiments, one of the signal features utilized for ice detection is the arrival time of guided waves propagating through the probe skin.

Yet another effect of ice accretion on the probe skin is the attenuation of the guided wave signal. As ice accretes, the attenuation of the signal will increase and the amplitude of the wave packet will be reduced. Directly monitoring the signal amplitude is an unreliable measure of ice accretion because said amplitude can be strongly affected by temperature, humidity, sensor aging, and other conditions in addition to the presence of ice accretion. However, the comparison of two or more subsequent wave packets propagating along path of increasing length in the probe skin can be an effective measure of attenuation in lieu of a direct amplitude measurement.

In some embodiments, one of the signal features utilized for ice detection is the attenuation of guided waves propagating through the probe skin. In some embodiments, said subsequent wave packets are multiple reverberations of the wave along one dimension of the probe. In other embodiments, said subsequent wave packets are due to the guided waves completing multiple trips around the circumference of the probe.

In other embodiments, additional signal features utilized for ice detection also include wave packet width in time and wave packet frequency bandwidth.

Figure 13C:
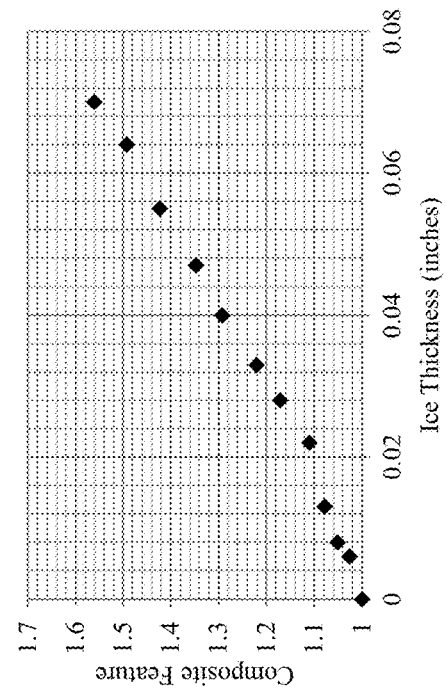
FIG. 13c illustrates the relationship between a composite feature value and accreted ice thickness for one embodiment of the ice sensing system.

In some embodiments, the ice detection algorithm utilizes an algebraic combination of multiple signal features to generate a single weighted feature vector that allows the algorithm to convert this multi-dimensional data into a single-dimension composite feature value. The amount of accreted ice can be determined by the amplitude of said composite feature value and the accretion rate of the ice can be determined by the rate of change of said composite feature value. FIG. 13c illustrates the relationship between a composite feature value and accreted ice thickness during a typical test.

A general equation for said algebraic combination of feature values is provided in equation (2), in which F represents the composite feature value, $f_i$ represents any one individual signal feature value, and $n_i$ represents a positive, negative, or zero factor applied to each respective signal feature value $f_i$ (i being any positive integer from 1 to the number of independent signal feature values included in the composite feature value calculation).

$$F = f_1^{n_1} \times f_2^{n_2} \times f_3^{n_3} \quad (2)$$

To make the system more robust, normalized feature values may be used in some embodiments in which relative changes in said feature values are monitored relative to their values at the time of system startup or over a predetermined time interval, which can help the system automatically adjust for environmental variation or other factors. Equation (3) describes said normalization, in which the bar notation indicates the "reference" value of the respective feature.

$$F = (f_1/\bar{f}_1)^{n_1} \times (f_2/\bar{f}_2)^{n_2} \times (f_3/\bar{f}_3)^{n_3} \quad (2)$$

Figure 14:
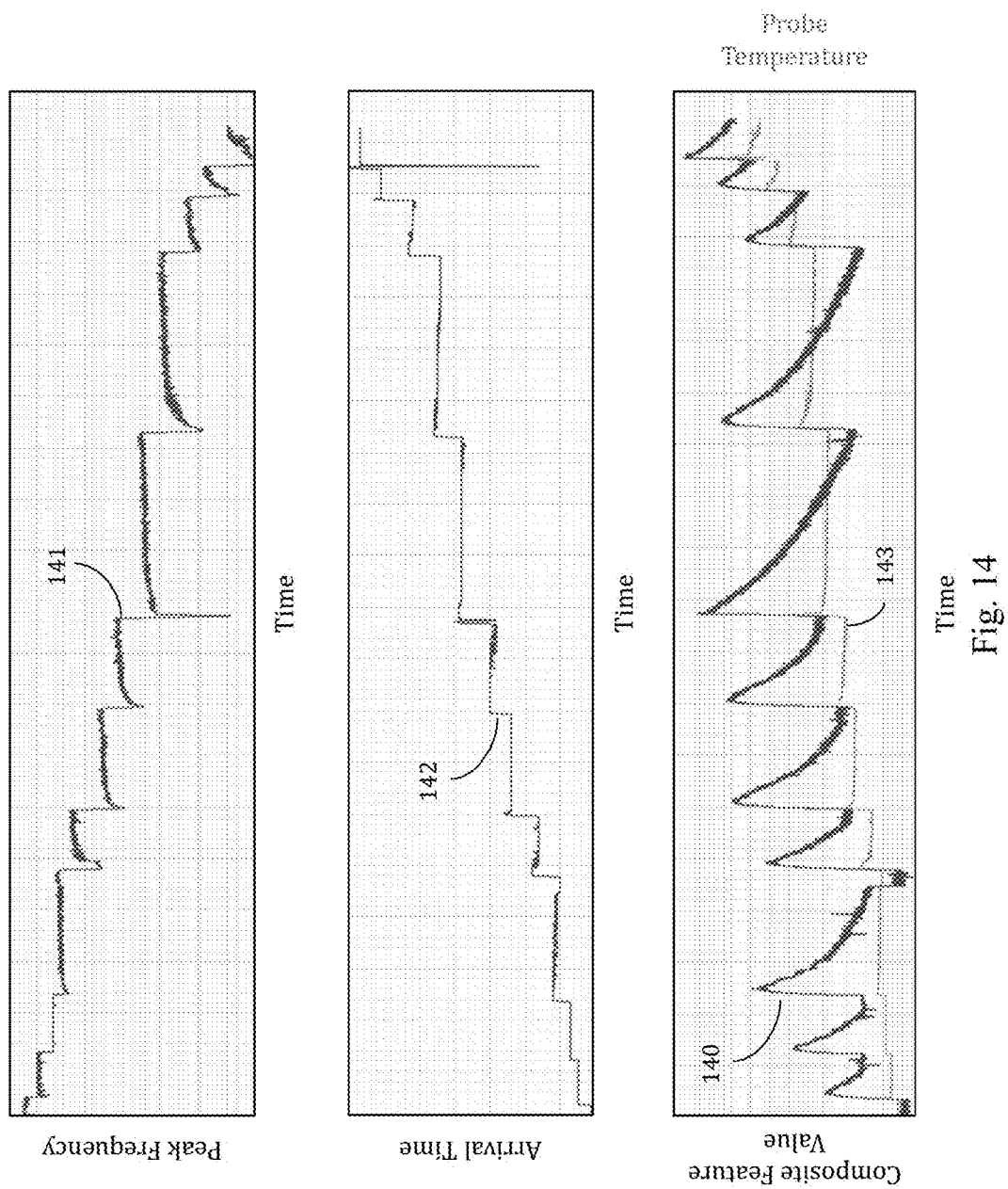
FIG. 14 is a series of plots illustrating the changes in various signal feature values as ice is accreted on one embodiment of the ice sensing probe.

FIG. 14 illustrates the response of various ice sensing signal features during ice accretion testing in accordance with some embodiments. During this test, ice was accreted by spraying cooled, atomized water on the surface of the ice sensing probe in a freezer environment. Each spray event corresponds to a rapid rise in temperature 140 which was monitored by means of a thermistor on the inside of the probe, and resulted in an increase in ice layer thickness of 0.004" to 0.006" per spray. Note that the rapid changes in the peak frequency 141 and arrival time 142 signal features correspond to the icing spray events and that a cumulative shift in said features, as well as the composite feature 143, occurs as ice accumulates on the probe throughout the course of the test.

FIG. 15 is a diagram illustrating the relationship of the components of one example of a controller 150 of an ice detection system in accordance with some embodiments. As shown FIG. 15, controller 150 includes one or more processors, such as processor(s) 152. Processor(s) 152 may be any central processing unit ("CPU"), microprocessor, microcontroller, or computational device or circuit for executing instructions and be connected to a communication infrastructure 154 (e.g., a communications bus, cross-over bar, or network). Various software embodiments are described in terms of this exemplary controller 150. After reading this description, it will be apparent to one of ordinary skill in the art how to implement the method using other computer systems or architectures.

In some embodiments, controller 150 includes a display interface 156 that forwards graphics, text, and other data from the communication infrastructure 154 (or from a frame buffer not shown) for display on a monitor or display unit 158 that is integrated with or separate from controller 150.

Controller 150 also includes a main memory 160, such as a random access memory ("RAM"), and a secondary memory 162. In some embodiments, secondary memory 162 includes a persistent memory such as, for example, a hard disk drive 164 and/or removable storage drive 166, representing an optical disk drive such as, for example, a DVD drive, a Blu-ray disc drive, or the like. In some embodiments, removable storage drive may be an interface for reading data from and writing data to a removable storage unit 168. Removable storage drive 166 reads from and/or writes to a removable storage unit 168 in a manner that is understood by one of ordinary skill in the art. Removable storage unit 168 represents an optical disc, a removable non-transitory memory device (such as an erasable programmable read only memory ("EPROM"), Flash memory, or the like), or a programmable read only memory ("PROM")) and associated socket, which may be read by and written to by removable storage drive 166. As will be understood by one of ordinary skill in the art, the removable storage unit 168 may include a non-transient machine readable storage medium having stored therein computer software and/or data.

Controller 150 may also include one or more communication interface(s) 170, which allows software and data to be transferred between controller 150 and external devices such as, for example, a server, computer, or other device. In some embodiments, communications interface 170 puts processor(s) 152 in communication with a heater (not shown) or other device for removing ice. Examples of the one or more communication interface(s) 170 may include, but are not limited to, a modem, a network interface (such as an Ethernet card or wireless card), a communications port, a Personal Computer Memory Card International Association ("PCMCIA") slot and card, one or more Personal Component Interconnect ("PCI") Express slot and cards, or any combination thereof. Software and data transferred via communications interface 170 are in the form of signals, which may be electronic, electromagnetic, optical, or other signals capable of being received by communications interface 170. These signals are provided to communications interface(s) 170 via a communications path or channel. The channel may be implemented using wire or cable, fiber optics, a telephone line, a cellular link, a radio frequency ("RF") link, or other communication channels.

In this document, the terms "computer program medium" and "non-transitory machine readable medium" refer to media such as removable storage units 168 or a hard disk installed in hard disk drive 164. These computer program products provide software to controller 150. Computer programs (also referred to as "computer control logic") may be stored in main memory 160 and/or secondary memory 162. Computer programs may also be received via communications interface(s) 170. Such computer programs, when executed by a processor(s) 152, enable the controller 150 to perform the features of the method discussed herein.

In an embodiment where the method is implemented using software, the software may be stored in a computer program product and loaded into controller 130 using removable storage drive 146, hard drive 144, or communications interface(s) 150. The software, when executed by a processor(s) 132, causes the processor(s) 132 to perform the functions of the method described herein. In another embodiment, the method is implemented primarily in hardware using, for example, hardware components such as application specific integrated circuits ("ASICs"). Implementation of the hardware state machine so as to perform the functions described herein will be understood by persons skilled in the art. In yet another embodiment, the method is implemented using a combination of both hardware and software.

Figure 15B:
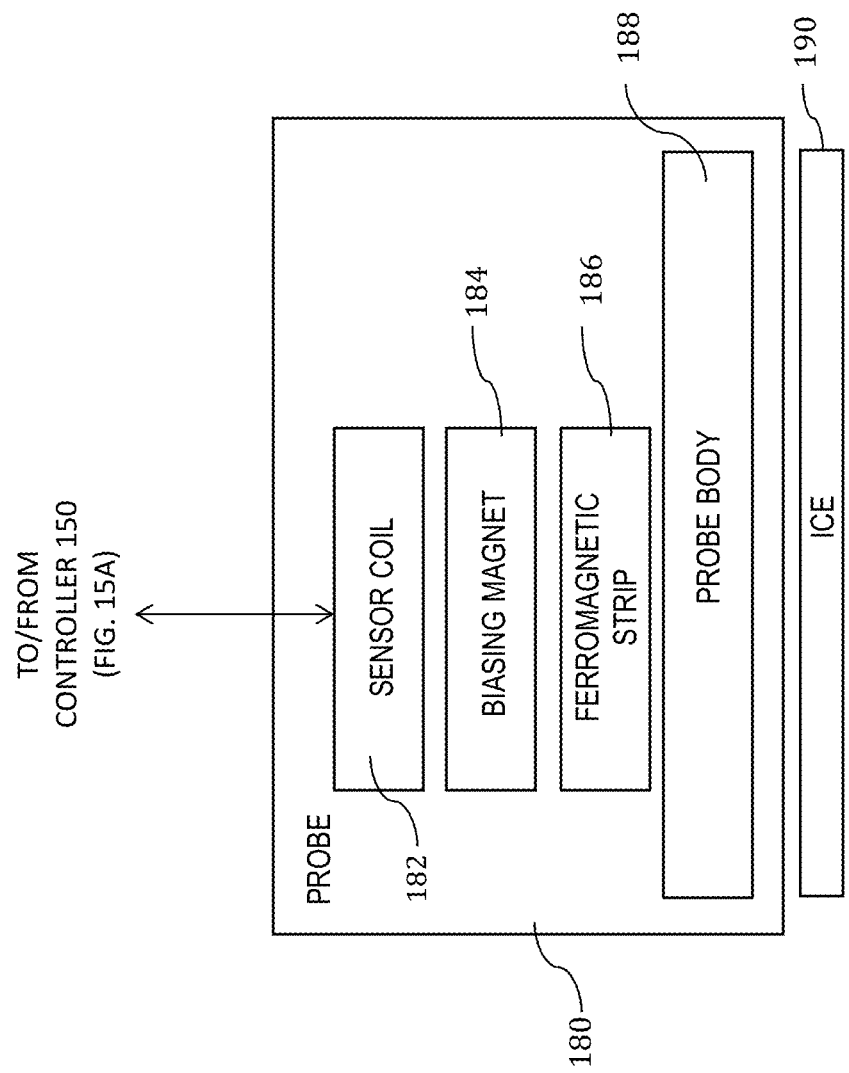

Controller 150 also includes a pulse generator 172 configured to output a variety of pulses to probe(s), such as probe 180 shown in FIG. 15B. For example, pulse generator 172 may transmit control signals to sensor coil 182 of probe 180.

An amplifier 174 is configured to amplify signals received from probe(s) 180. Such signals received by probe 180 include reflections of guided waves from ice formed on a structure, such as a wing of an airplane, in response to guided wave signals transmitted by pulse generator 172 to probe(s) 180. An analog-to-digital ("A/D") converter 176 is coupled to an output of amplifier 174 and is configured to convert analog signals received from amplifier 174 to digital signals. The digital signals output from A/D converter 176 may be transmitted along communication infrastructure 154 where they may undergo further signal processing by processor(s) 152 as will be understood by one of ordinary skill in the art.

As shown in FIG. 15B, sensor coil 182 of probe 180 is disposed adjacent to a biasing magnet 184 and ferromagnetic strip 186. Ferromagnetic strip 186 (and the other components of probe 180) is supported by probe body 188 on which ice 190 may be formed.

In some embodiments, multiple ice sensing probes may be distributed across the aircraft or other engineered structure, and in such embodiments the electronic pulser/receiver system may take one of several forms. In some embodiments, the pulser/receiver system is a multi-channel system that is capable of simultaneously and independently applying alternating current signals to the at least one ice sensor coil and measuring the current induced by received guided wave signals at the at least one ice sensor coil. In additional embodiments, the pulser/receiver system is a multiplexed single-channel system that is capable of applying alternating current signals to one ice sensor coil at a time and measuring the current induced by received guided wave signals at one ice sensor coil at a time and subsequently repeating this measurement for each of the ice sensor coils in turn.

Figure 16:
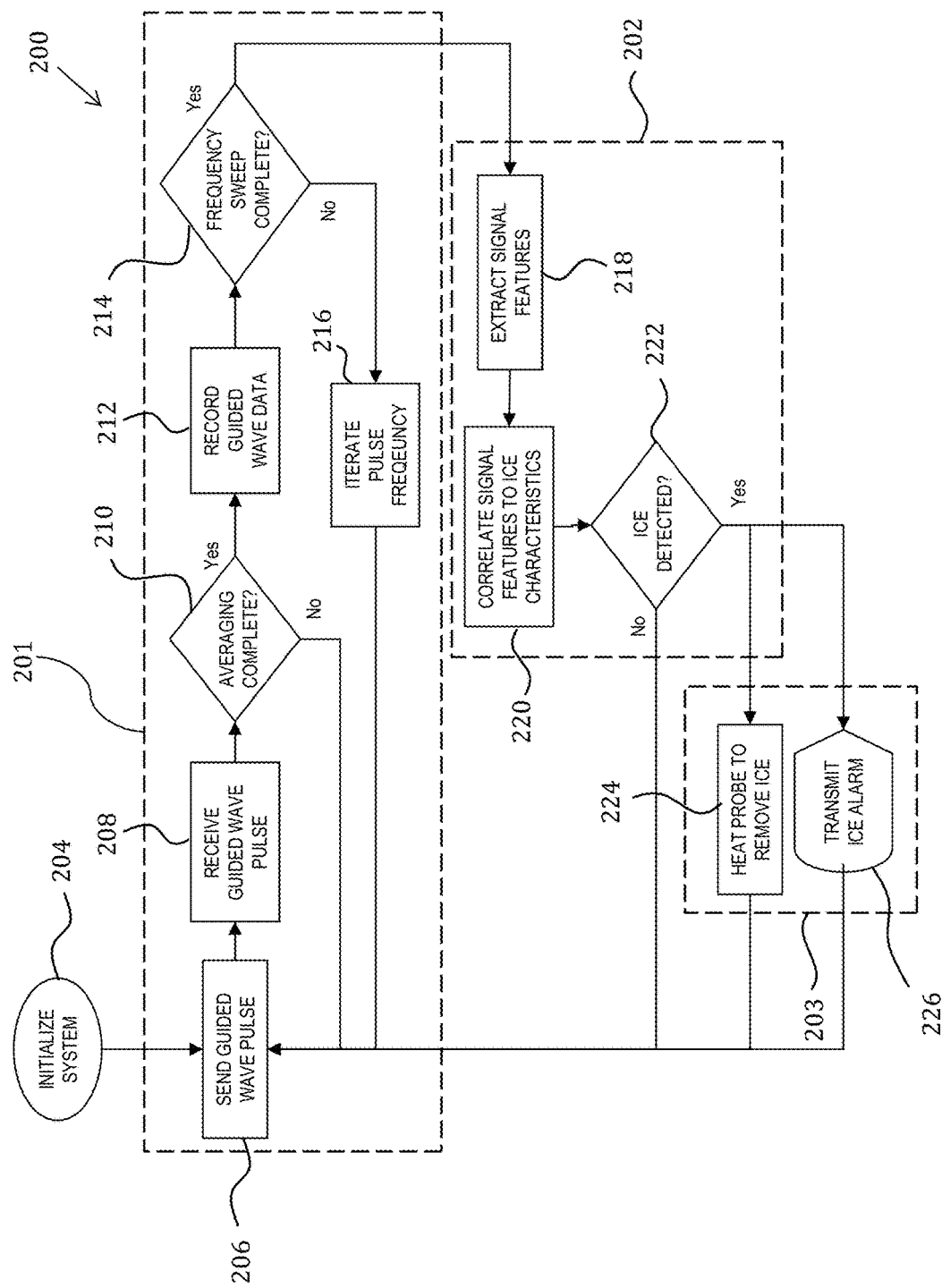
FIG. 16 is a diagram of one embodiment of an ice sensing algorithm.

FIG. 16 is a diagram of one embodiment of an ice sensing algorithm 200, which includes a guided wave pulse-detect cycle 201, a signal processing algorithm 202, and an icing response algorithm 203. Once the system is initialized at block 204, the guided wave pulse-detect cycle 201 includes generating guided waves in the probe body at block 206. In some embodiments, the guided waves are generated by processor(s) 152 of controller 150 causing pulse generator 172 (FIG. 15A) to send signals to sensor coil 182 (FIG. 15B).

At block 208 of FIG. 16, guided wave signals are received. In some embodiments, such as embodiments of a probe in a pulse-echo configuration, the guided wave signals transmitted by sensor coil 182 of probe 180 are received by the same sensor coil (FIG. 15B). In some embodiments, such as embodiments of a probe in a pitch/catch configuration, the guided wave signals are the guided waves transmitted by the first coil that are received by a second coil.

At decision block 210, processor(s) 152 average the signal information, additionally, processor(s) 152 determine whether averaging is complete based on pre-determined algorithm settings. If the decision is no, then sensing algorithm 201 moves to block 206. If the decision is yes, then the algorithm moves to block 212 where the guided wave data are stored in a non-transitory machine readable storage medium, such as memory 160 and/or memory 162.

At decision block 214, a determination is made as to whether a frequency sweep is complete based on pre-determined algorithm settings. If the answer is no, then the algorithm moves to block 216 where the pulse frequency is iterated. In some embodiments, sensing algorithm 201 is iterated over at least one center pulse frequency. If the answer at decision block 214 is yes, then the sensing algorithm 201 is complete and algorithm 200 moves to signal processing algorithm 202.

At block 218, signal features are extracted from the guided wave data. Such signal feature extraction can include, but is not limited to, extraction of the optimum transmission frequency, wave arrival time, and wave attenuation.

At block 220, the signal features are correlated to icing characteristics include the presence, thickness, and accretion rate of any ice present on a surface of the probe.

At decision block 222, a determination is made as to whether ice is present on the probe. As described above, the determination is made by analyzing the signal features to the ice characteristics to determine changes to the dispersion curve and/or changes to other signal features. If ice is not detected, then algorithm 200 moves back to guided wave pulse detection cycle 201. If ice is detected, then algorithm moves to an icing response algorithm 203.

In some embodiments, icing response algorithm 203 includes causing the probe surface to be heated at block 224. For example, processor(s) 152 can cause a heater (not shown) to be turned on by causing a signal to be transmitted over communications interface 170. Additionally or alternatively, an alarm or other user notification can be generated at block 226. Examples of such alarms include, but are not limited, an audible signal, a visual signal, and/or a tactile signal. An audible signal can be generated by a horn or speaker, and a visual signal can be a flashing light or a message displayed on display 158. In some embodiments, a text or email message can be generated. A tactile signal can include causing a buzzer or vibratory device to be actuated. A person of ordinary skill in the art will understand that other signals or steps can be taken in icing response algorithm 293. Further, a person of ordinary skill in the art will understand that certain steps of algorithm 200 can be performed concurrently, and that algorithm can be repeated any number of times.

The foregoing outlines features of several embodiments so that those skilled in the art may better understand the aspects of the present disclosure. Those of ordinary skill in the art should appreciate that they may readily use the present disclosure as a basis for designing or modifying other processes and structures for carrying out the same purposes and/or achieving the same advantages of the embodiments introduced herein. Those of ordinary skill in the art should also realize that such equivalent constructions do not depart from the spirit and scope of the present disclosure, and that they may make various changes, substitutions, and alterations herein without departing from the spirit and scope of the present disclosure.

What is claimed is:

1. A system for detecting ice accretion, comprising:
    a probe having body that defines an internal chamber;
    at least one magnetostrictive guided wave sensor for generating and receiving shear horizontal-type guided waves disposed within the internal chamber of the body of the probe, said magnetostrictive guided wave sensor comprising:
        a ferromagnetic strip extending parallel to a length of the body of the probe;
        at least one sensor coil disposed adjacent to said ferromagnetic strip within the internal chamber of the body; and
        at least one biasing magnet disposed adjacent to the ferromagnetic strip and configured to induce a biasing magnetic field in said ferromagnetic strip; and
    a controller including a processor in signal communication with the at least one magnetostrictive guided wave sensor, the processor configured to:
        cause the at least one magnetostrictive guided wave sensor to generate guided waves in the body of the probe;
        extract at least one signal feature from a guided wave signal received by the at least one magnetostrictive guided wave sensor; and
        determine at least one characteristic of ice accreted on an outer surface of said body of the probe.

2. The system of claim 1, where the at least one sensor coil includes a printed circuit board having a meandering coil formed thereon.

3. The system of claim 1, wherein said at least one biasing magnet includes at least one of a permanent magnet and an electromagnet.

4. The system of claim 1, wherein said ferromagnetic strip includes an iron-cobalt alloy.

5. The system of claim 1, wherein said probe body includes a magnesium alloy.

6. The system of claim 1, wherein said probe body includes a carbon fiber-reinforced polymer.

7. The system of claim 1, wherein said at least one sensor coil is configured such that said guided waves propagate along the probe body in one of a longitudinal direction and a lateral direction.

8. The system of claim 1, wherein said at least one sensor coil is configured such that said guided waves are propagated circumferentially around said probe body.

9. The system of claim 1, wherein said at least one sensor coil is configured to generate said guided waves and to receive the guided wave signal in a pulse-echo configuration.

10. The system of claim 1, wherein said at least one sensor coil includes a first sensor coil and a second sensor coil, the first sensor coil configured to generate said guided waves and the second sensor coil is configured to receive said guided wave signal in a pitch-catch configuration.

11. The system of claim 1, wherein said probe has a cross-sectional shape that is one of an airfoil shape, a circular shape, and an elliptical shape and is mounted to an external surface of a structure that may be exposed to icing conditions.

12. The system of claim 1, wherein said probe is configured to be mounted flush to a surface of a structure.

13. The system of claim 1, further comprising a heating element for at least one of melting and ablating ice from a surface of said body of the probe.

14. A method for the detection of ice accretion, comprising:
    generating a time-varying current in at least one magnetostrictive coil to induce a time-varying magnetization in a ferromagnetic strip in the presence of a biasing magnetic field to generate shear horizontal-type guided waves in a body of a probe housing the at least one magnetostrictive coil, the ferromagnetic strip, and a biasing magnet in an internal chamber of the body of the probe, the ferromagnetic strip extending parallel to a longitudinal direction of the body of the probe;
    detecting a guided wave signal by the at least one magnetostrictive coil;
    extracting at least one signal feature, including at least one of optimum transmission frequency, wave packet arrival time, and wave attenuation, from the guided wave signal; and
    correlating said at least one signal feature with at least one characteristic of ice accreted on an outer surface of said body of the probe.

15. The method of claim 14, wherein the generating, detecting, and extracting steps are performed across a range of frequencies by successively applying said time-varying current with more than one pulse center frequency.

16. The method of claim 14, wherein the generating, detecting, and extracting steps are performed across a range of frequencies by applying said time-varying current with a broadband pulse.

17. The method of claim 14, further comprising algebraically combining the at least one signal feature into a composite feature value for correlating with at least one at least one characteristic of ice accreted on an outer surface of the body of said probe.

18. The method of claim 14, further comprising normalizing said at least one signal by a reference value in order to overcome variability due to environmental or degradation factors.

19. The method of claim 14, further comprising correlating an amplitude of said at least one feature value with a thickness of ice accreted on said probe.

20. The method of claim 14, further comprising correlating a rate of change of said at least one feature value with a rate of accretion of ice on said probe.

21. The method of claim 14, further comprising heating said probe to at least one of melt and ablate ice accreted on said probe after said ice is detected.

* * * * *